(12) United States Patent
Mattheakis et al.

(10) Patent No.: US 7,235,353 B2
(45) Date of Patent: *Jun. 26, 2007

(54) PREDICTING HEPATOTOXICITY USING CELL BASED ASSAYS

(75) Inventors: Larry C. Mattheakis, Cupertino, CA (US); Jay Kenneth Trautman, Los Altos, CA (US); Gregg Peter Solar, San Anselmo, CA (US); Jinhong Fan, San Mateo, CA (US); Eugeni Vaisberg, Foster City, CA (US); Cynthia Lynn Adams, San Carlos, CA (US); Aibing Rao, Burlingame, CA (US)

(73) Assignee: Cytokinetics, Inc., South San Francisco, CA (US)

( * ) Notice: Subject to any disclaimer, the term of this patent is extended or adjusted under 35 U.S.C. 154(b) by 584 days.

This patent is subject to a terminal disclaimer.

(21) Appl. No.: 10/623,486

(22) Filed: Jul. 18, 2003

(65) Prior Publication Data

US 2005/0014216 A1    Jan. 20, 2005

(51) Int. Cl.
*C12Q 3/00* (2006.01)
*C12Q 1/68* (2006.01)
*C12Q 1/26* (2006.01)
*C12Q 1/04* (2006.01)
*C12N 5/00* (2006.01)

(52) U.S. Cl. .................. 435/3; 435/6; 435/25; 435/34; 435/40.5; 435/325; 435/370; 435/455

(58) Field of Classification Search .................. 435/3, 435/6, 25, 34, 40.5, 325, 370, 455; 702/20
See application file for complete search history.

(56) References Cited

U.S. PATENT DOCUMENTS

| | | |
|---|---|---|
| 4,818,710 A | 4/1989 | Sutherland et al. |
| 4,922,092 A | 5/1990 | Rushbrooke et al. |
| 4,959,301 A | 9/1990 | Weaver et al. |
| 4,965,725 A | 10/1990 | Ruttenberg |
| 5,162,990 A | 11/1992 | Odeyale et al. |
| RE34,214 E | 4/1993 | Carlsson et al. |
| 5,287,272 A | 2/1994 | Rubbenberg et al. |
| 5,326,691 A | 7/1994 | Hozier |
| 5,355,215 A | 10/1994 | Schroeder et al. |
| 5,526,258 A | 6/1996 | Bacus |
| 5,548,661 A | 8/1996 | Price et al. |
| 5,655,028 A | 8/1997 | Soll et al. |
| 5,733,721 A | 3/1998 | Hemstreet, III et al. |
| 5,741,648 A | 4/1998 | Hemstreet, III et al. |
| 5,776,748 A | 7/1998 | Singhvi et al. |
| 5,790,692 A | 8/1998 | Price et al. |
| 5,790,710 A | 8/1998 | Price et al. |
| 5,804,436 A | 9/1998 | Okun et al. |
| 5,856,665 A | 1/1999 | Price et al. |
| 5,893,095 A | 4/1999 | Jain et al. |
| 5,919,646 A | 7/1999 | Okun et al. |
| 5,932,872 A | 8/1999 | Price |
| 5,962,250 A | 10/1999 | Gavin et al. |
| 5,976,825 A | 11/1999 | Hochman |
| 5,989,835 A | 11/1999 | Dunlay et al. |
| 5,991,028 A | 11/1999 | Cabib et al. |
| 5,995,143 A | 11/1999 | Price et al. |
| 6,007,996 A | 12/1999 | McNamara et al. |
| 6,008,010 A | 12/1999 | Greenberger et al. |
| 6,083,763 A | 7/2000 | Balch |
| 6,103,479 A | 8/2000 | Taylor |
| 6,146,830 A | 11/2000 | Friend et al. |
| 6,222,093 B1 | 4/2001 | Marton et al. |
| 6,345,115 B1 | 2/2002 | Ramm et al. |
| 6,423,491 B1* | 7/2002 | Howe et al. .................. 435/6 |
| 6,852,845 B1* | 2/2005 | Rothberg et al. .......... 536/23.1 |
| 7,041,501 B2* | 5/2006 | Flint et al. .................. 435/370 |
| 2002/0141631 A1 | 10/2002 | Vaisberg et al. |
| 2002/0154798 A1 | 10/2002 | Cong et al. |
| 2003/0224407 A1* | 12/2003 | Bertram et al. ................. 435/6 |

FOREIGN PATENT DOCUMENTS

| | | |
|---|---|---|
| EP | 0 468 705 A2 | 1/1992 |
| EP | 0 317 139 B1 | 11/1995 |
| EP | 0 902 394 A1 | 3/1999 |
| WO | WO 87/02802 | 5/1987 |
| WO | WO 93/21511 | 10/1993 |
| WO | WO 94/11841 | 5/1994 |
| WO | WO 95/22749 | 8/1995 |
| WO | WO 96/01438 | 1/1996 |

(Continued)

OTHER PUBLICATIONS

Mattheakis et al., PCT Search Report for Int'l Application No. PCT/US2004/022970, Int'l Filing Date Jul. 15, 2004, dated Dec. 1, 2004.

(Continued)

*Primary Examiner*—Herbert J. Lilling
(74) *Attorney, Agent, or Firm*—Beyer Weaver LLP

(57) ABSTRACT

Cell based assays are used to assess the hepatotoxicity of a stimulus. Imaging technologies are used to analyze the effects of a stimulus on hepatocytes. Image analysis may characterize the stimulus on the basis of whether it is hepatotoxic, and if so what type of pathology is exhibited; e.g., apoptosis, necrosis, cholestasis, and/or steatosis.

19 Claims, 7 Drawing Sheets

FOREIGN PATENT DOCUMENTS

| | | |
|---|---|---|
| WO | WO 96/09605 | 3/1996 |
| WO | WO 97/20198 | 6/1997 |
| WO | WO 97/40055 | 10/1997 |
| WO | WO 97/43732 | 11/1997 |
| WO | WO 97/45730 | 12/1997 |
| WO | WO 98/05959 | 2/1998 |
| WO | WO 98/35256 | 8/1998 |
| WO | WO 98/38490 | 9/1998 |
| WO | WO 98/44333 | 10/1998 |
| WO | WO98/45704 | 10/1998 |
| WO | WO 98/52018 | 11/1998 |
| WO | WO99/05323 | 2/1999 |
| WO | WO99/08091 | 2/1999 |
| WO | WO99/17116 | 4/1999 |
| WO | WO 99/39184 | 8/1999 |
| WO | WO 99/44062 | 9/1999 |
| WO | WO 99/54494 | 10/1999 |
| WO | WO 99/67739 | 12/1999 |
| WO | WO00/03246 | 1/2000 |
| WO | WO 00/06774 | 2/2000 |
| WO | WO 00/17624 | 3/2000 |
| WO | WO00/17643 | 3/2000 |
| WO | WO 00/17808 | 3/2000 |
| WO | WO 00/26408 | 5/2000 |
| WO | WO 00/29984 | 5/2000 |
| WO | WO 00/31534 | 6/2000 |
| WO | WO00/33250 | 6/2000 |
| WO | WO00/43820 | 7/2000 |
| WO | WO00/49540 | 8/2000 |
| WO | WO00/50872 | 8/2000 |
| WO | WO 00/60356 | 10/2000 |
| WO | WO 00/70528 | 11/2000 |
| WO | WO0135072 A2 | 5/2001 |
| WO | WO 95/10036 | 4/2005 |

OTHER PUBLICATIONS

Mattheakis et al., PCT Written Opinion for Int'l Application No. PCT/US2004/022970, Int'l Filing Date Jul. 15, 2004.
Towner et al., "Non-Invasive in Vivo Magnetic Resonance Imaging Assessment of Acute Aflatoxin B1 Hepatotoxicity in Rats", BBA-General Subjects, Elsevier Science Publishers, NL, vol. 1475, No. 3, Jul. 26, 2000, pp. 314-320.
Sturgeon et al., "In Vivo Assessment of Microcystin-LR-induced Hepatoxicity in the rat using proton nuclear magnetic rezsonance ($^1$H-NMR) Imaging" BBA- General Subjects, Biochemica et Biophysica Acta 1454 (1999) pp. 227-235.
Sakai et al., Rapid and Sensitive Neurotoxicity Test Based on the Morphological Changes of PC12 Cells with Simple Computer-Assisted Image Analysis, Journal of Bioscience and Bioengineering, vol. 90, No. 1, 20-24. 2000.
Hall et al., "Two Methods of Assessment of Methotrexate Hepatotoxicity in Patients with Rheumatoid Arthritis", Annals of the Rheumatic Diseases 1991, vol. 50, No. 7, pp. 471-476.
Molinari et al., "Automated Image Analysis for Monitoring Oxidative Burst in Macrophages", Analytical and Quantitative Cytology and Histology, vol. 22, No. 5, Oct. 2000, pp. 423-427.
Kapur et al., "Design and Fabrication of Spatially Controlled Miniaturized Organ Systems from Stem Cells", U.S. Appl. No. 60/127,339, filed Apr. 1, 1999.
Adams et al., "Cell Patterning on Glass and Polymeric Substrates", U.S. Appl. No. 60/138,119, filed Jun. 7, 1999.
Dunlay et al., "Data Management and Presentation Methods", U.S. Appl. No. 60/140,240, filed Jun. 21, 1999.
Blankenstein et al., Modular concept of a laboratory on a chip for chemical and biochemical analysis, © 1998, Biosensors & Bioelectronics, vol. 13., No. 3-4, pp. 427-438.
István Cseke, "A Fast Segmentation Scheme for White Blood Cell Images", © 1992 IEEE, pp. 530-533.
Hofland et al., "Role of Tumor-Derived Fibroblasts in the Growth of Primary Cultures of Human Breast-Cancer Cells: Effects of Epidermal Growth Factor and the Somatostatin Analogue Octreotide", © 1995 Wiley-Liss, Inc., Publication of the International Union Against Cancer, pp. 93-99.
Boyce et al., "Systems and Methods to Achieve Integrated Presentation of Summary Statistics, Detail Measurements, and Raw Images While Maintaining Efficient Use of Storage Media Through Separation of the Data in an Integrated Data Management and Presentation System", U.S. Appl. No. 60/108,291, filed Nov. 13, 1998.
Boyce et al., "Data Management and Presentation Methods", U.S. Appl. No. 60/142,375, filed Jul. 6, 1999.
Boyce et al., "Data Management and Presentation Methods", U.S. Appl. No. 60/142,646, filed Jul. 6, 1999.
Roger James, "A Pulsed Polarimeter", U.S. Appl. No. 60/110,643, filed Dec. 1, 1998.
Wang et al., "Database for Storage, Retrieval, and Analysis of Cellular Information", U.S. Appl. No. 60/120,801, filed Feb. 19, 1999.
Printout from Q3DM Website (www.Q3DM.com), printed on Mar. 1, 2001, 30 pages.
Printout from Automated Cell Website (www.automatedcell.com), printed on Mar. 9, 2001, 24 pages.
Pauwels, et al., "Determination of the Mechanism of Action of Anticancer Drugs by Means of the Computer-Assisted Microscope Image Analysis of Feulgen-Stained Nuclei", J. Pharmacological and Toxicological Methods, 37: 105-115 (1997).
Pauwels, et al., "Monitoring of chemotherapy-induced morphonnuclear modification by means of digital cell-image analysis", I. Cancer Res. Clin. Oncol., 119: 533-540 (1993).
Pauwels, et al., "In Vitro Digital Cell Image Analysis of Morphonuclear Modifications Induced by Natural DNA-Interacting Anticancer Drugs in Three Neoplastic Cell Lines", Meth. Find. Exp. Clin. Pharmacol, 17(3): 151-162 (1995).
Pauwels, et al., "The Application of Computerized Analysis of Nuclear Images and Multivariate Analysis to the Understanding of the Effects of Antineoplastic Agents and Their Mechanism of Action", Meth. Find. Exp. Clin Pharmacol, 15(2): 113-124 (1993).
Pauwels, et al., "Combination of Computerized Morphonuclear and Multivariate Analysis to Characterize In Vitro the Antineoplastic Effect of Alkylating Agents", J. Pharmacol. and Toxicol. Methods, 33(1): 34-45 (1995).
Stearns et al., Interleukin 10 (IL-10) Inhibition of Primary Human Prostate Cell-induced Angiogenesis: IL-10 Stimulation of Tissue Inhibitor Metalloproteinase-1 and Inhibition of Matrix Metalloproteinase (MMP)-2/MMP-9 Secretion, (1999) Clin. Cancer Res. 5: 189-196.
Sundblad, et al., "The use of image analysis and automation for measuring mitotic index in apical conifer meristems", Oct. 1998, Journal of Experimental Botany, vol. 49, No. 327, pp. 1749-1756.
Takayama et al., "Patterning cells and their environments using multiple laminar fluid flows in capillary networks", (1999) Proc. Natl., Acad. Sci USA, 96:5545-5548.
Weinstein, et al., "An Information-Intensive Approach to the Molecular Pharmacology of Cancer", Science, 275: 343-349 (Jan. 17, 1997).
Hartwell, et al., "Integrating Genetic Approaches into the Discovery of Anticancer Drugs", (1997) Science 278:1064-1068.
Ng et al., "Evaluating Multi-Dimensional Indexing Structures for Images Transformed by Principal Component Analysis", Proceedings of SPIE, Bellingham, Spie, US (1996), vol. 2670, pp. 50-61.
Boland et al., "Automated Recognition of Patterns Characteristic of Subcellular Structures in Fluorescence Microscopy Images", Rapid Communications, Cytometry 33:366-375 (1998).
Giuliano et al., "High-Content Screening: A New Approach to Easing Key Bottlenecks in the Drug Discovery Process", © 1997 The Society for Biomolecular Screening, Inc., Journal of Biomolecular Screening, vol. 2, No. 4, 1997, pp. 249-258.
Montironi et al. "Computed cell cycle and DNA histogram analyses in image cytometry in breast cancer", 1993, pp. 795-800.
Giuliano et al., "Fluorescent-protein biosensors: new tools for drug discovery", Mar. 1998, vol. 16, pp. 135-140.

Kobayashi N, et al., "Prevention of acute liver failure in rats with reversibly immortalized human hepatocytes", Science, vol. 287, Feb. 18, 2000, 1258-1262.

Lieber, C.S., "Alcohol and liver: metabolism of alcohol and its role in hepatic and extrahepatic diseases, The Mount Sinai Journal of Medicine", vol. 67, No. 1, Jan. 2000, pp. 84-94.

Baroana, E., et al., "Alcoholic hepatomegaly: accumulation of protein in the liver", Science, vol. 190, 1975, pp. 794-795.

Tuchweber, B., et al., "Mechanisms Of Experimentally Induced Intrahepatic Cholestasis", Progress in Liver Diseases, (1986), pp. 161-178.

McMillian, et al., "Nile Red Binding to HepG2 Cells: An Improved Assay for In Vitro Studies of Hepatosteatosis", In Vitro & Molecular Toxicology, vol. 14, No. 3, 2001, pp. 177-190.

Watanabe, S. et al., "Phalloidin Alters Bile Canalicular Contractility In Primary Monalayer Cultures Of Rat Liver", Gastroenterology, (1983), 85, pp. 245-253.

Thibault, et al., "Actin filament alteration as a potential marker for cholestasis: a study in isolated rat hepatocyte couplets", Toxicology, 73, (1992), pp. 269-279.

Fowler, S.D., et al., "Application Of Nile Red, A Fluorescent Hydrophobic Probe, For The Detection Of Neutral Lipid Deposits In Tissue Sections: Comparison With Oil Red O," J Histochem Cytochem, Mar. 1985, vol. 33, No. 8, pp. 833-836.

Greenspan, P., et al., "Nile Red: A Selective Fluorescent Stain For Intracellular Lipid Droplets," J Cell Biol, 1985, vol. 100, No. 3, pp. 965-973.

Amacher, D.E., "A toxicologist's guide to biomarkers of hepatic response", Hum Exp Toxicol, 2002, 21(5): p. 253-262.

Amacher, D.E., et al., "Tetracycline-Induced Steatosis In Primary Canine Hepatocyte Cultures," Fundam Appl Toxicol, 1997, 40(2): p. 256-263.

Kutsyy et al., "Methods and Apparatus for Investigating Side Effects", U.S. Appl. No. 10/621,821, filed Jul. 16, 2003.

Vaisberg et al., "Characterizing Biological Stimuli By Response Curves", U.S. Appl. No. 09/789,595, filed Feb. 20, 2001.

Crompton et al., "A Database Method for a Predicitive Cellular Bioninformatics," U.S. Appl. No. 09/310,879, filed May 14, 1999.

Crompton et al., "Database System Including Computer For Predicitive Cellular Bioninformatics," U.S. Appl. No. 09/311,996, entitled filed May 14, 1999.

Crompton et al., "A Database System For Predicitive Cellular Bioninformatics," U.S. Appl. No. 09/311,890, filed May, 1999.

Vaisberg, et al., "Image Analysis Of The Golgi Complex", U.S. Appl. No. 09/792,012, filed Feb. 20, 2001.

Coleman et al., "Methods and Apparatus For Characterising Cells And Treatments", U.S. Appl. No. 10/615,116, filed Jul. 7, 2003.

Cong et al., "Extracting Shape Information Contained In Cell Images", U.S. Appl. No. 09/792,013, filed Feb. 20, 2001.

Serbouti, et al., "Image Segmentation and Classification Methods to Detect Leukemias", (1991) Annual Int'l Conf. of IEEE Eng. In Medicine & Biology Soc., vol. 13, No. 1, pp. 0260-0261.

Vaisberg et al., "Classifying Cells Based on Information Contained In Cell Images", U.S. Appl. No. 09/729,754, filed Dec. 4, 2000.

Vaisberg, et al., "Characterizing Biological Stimuli By Response Curves," U.S. Appl. No. 09/789,595, filed Feb. 20, 2001.

Rubas et al., "An Integrated Method to Determine Epithelial Transport and Bioactivity of Oral Drug Candidates in Vitro", Rapid Communication, Pharmaceutical Research, vol. 13, No. 1, 1996, pp. 23-26.

Nilsson, et al., "Segmentation of Dense Leukocyte Clusters", IEEE Workshop on Mathematical Methods in Biomedical Image Analysis, 2001, pp. 221-227.

Malpica et al., "Applying Watershed Algorithms to the Segmentation of Clustered Nuclei", Cytometry, vol. 28, 1997, pp. 289-297.

Ancin, et al., "Advances in Automated 3-D Image Analysis of Cell Populations Imaged by Confocal Microscopy", Cytometry, vol. 25, 1996, pp. 221-234.

Blom, et al., "Regional loss of the mitochondrial membrane potential in the hepatocyte is rapidly followed by externalization of phosphatidyl serines at that specific site during apoptosis", JBC Papers in Press, published on Jan. 21, 2003, pp. 1-36.

Uria, et al., "Regulation of Collagenase-3 Expression in Human Breast Carinomas Is Mediated by Stromal-Epithelial Cell Interactions", Cancer Research 57, Nov. 1, 1997, pp. 4882-4888.

Zimmerman, H.J., "Expressions of Hepatotoxicity", Hepatotoxixity: The Adverse Effects of Drugs and Other Chemicals on the Liver, Section I, General Considerations, $2^{nd}$ Edition, 1999, pp. 61-109.

Zimmerman, H.J., "Classification of Hepatotoxins and Mechanisms of Toxicity", Hepatotoxixity: The Adverse Effects of Drugs and Other Chemicals on the Liver, Section I, General Considerations, $2^{nd}$ Edition, 1999, pp. 111-145.

Zimmerman, H.J., "Experimental Hepatotoxixity", Hepatotoxixity: The Adverse Effects of Drugs and Other Chemicals on the Liver, Section II, General Considerations, $2^{nd}$ Edition, 1999, pp. 201-228.

Zimmerman, H.J., "Toxic Cholestasis", Hepatotoxixity: The Adverse Effects of Drugs and Other Chemicals on the Liver, Section II, General Considerations, $2^{nd}$ Edition, 1999, pp. 295-323.

D.L. Taylor, "The new vision of light microscopy", American Scientist 80:322-335, 1992.

K. A. Giuliano et al., "Measurement and manipulation of cytoskeletal dynamics in living cells", Current Opinion in Cell Biology 7:4-12, 1995.

BioDx, Internet Archive Way-Back Machine, Feb. 4, 1997 From website www.biodx.com.

A. Waggoner et al., "Multiparameter Fluorescence imaging microscopy: re-agents and instruments" Human Pathology, vol. 27, No. 5, 494-502, 1996.

Benveniste et al., "Characterization of Internalization and endosome formation of epidermal growth factor in transfected NIH-3T3 cells by computerized image-intensified three-dimensional fluorescence microscopy", The Journal of Cell Biology 109: 2105-2115, 1989.

K.L. Carey et al., "Evidence using a green fluorescent protein-glucocorticoid receptor chimera that the RAN/TC4 GTPase mediates an essential function independent of nuclear protein import", The Journal of Cell Biology, vol. 133, No. 5, 985-996, 1996.

J. Kolega et al., "Quantitation of cytoskeletal fibers in fluorescence images: stress fiber disassembly accompanies dephosphorylation of the regulatory light chains of myosin II", Bioimaging 1:136-150, 1993.

D.L Farkas et al., "Multimode light microscopy and the dynamics of molecules, cells, and tissues", Annu. Rev. Physiol. 55:785-817, 1993.

W. Böcker et al., "Automated cell cycle analysis with fluorescent microscopy and image analysis", Phys. Med. Biol. 41:523-537, 1996.

R. Pepperkok et al., "System for quantitation of gene expression in single cells by computerized microimaging: Application to c-*fos* expression after microinjection of anti-casein kinase II antibody", Experimental Cell Research 204:278-285, 1993.

F. Hanakam, "Myristoylated and non-myristoylated forms of the pH sensor protein hisactophilin II: intracellular shuttling to plasma membrane and nucleus monitored in real time by a fusion with green fluorescent protein", The EMBO Journal 15(12):2935-43, 1996.

N.B. Cole, "Golgi Dispersal during microtubule disruption: Regeneration of Golgi stacks at Peripheral Endoplasmic Reticulum Exit sites," Molecular Biology of the Cell, vol. 7, 631-650, 1996.

B.M. Machiels Subcellualr localization of proteasomes in apoptotic lung tumor cells and persistence as compared to intermediate filaments European Journal of Cell Biology 70:250-259, 1996.

N. Yasuhara et al., "Essential Role of active nuclear transport in apoptosis" Genes to Cells 2:55-64, Jan. 1997.

BioDx, Inc., Internet archive, way back machine May 21, 1997 From website www.biodx.com.

M.V. Rogers, "Light on high -throughput screening: fluorescence-based assay technologies", Drug Discovery Today, vol. 2, No. 4, 156-160 Apr. 1997.

W. Böcker et al., "Image Processing algorithms for the automated micronucleus assay in binucleated human lymphocytes", Cytometry 19:283-294 (1995).

Lansing D. Taylor, U.S. Appl. No. 60/018,696, filed May 30, 1996.

\* cited by examiner

PREDICTING HEPATOTOXICITY USING CELL BASED ASSAYS

BACKGROUND

I. Field of the Invention

The present invention relates to methods and apparatus for assessing the hepatotoxicity of a stimulus. More particularly, the present invention relates to image analysis methods and apparatus that characterize a stimulus based upon phenotypic characteristics of hepatocytes and some other cell types exposed to the stimulus.

II. Background

Hepatotoxicity is a major safety concern for drug development. Approximately 90 percent of lead candidates fail to become drugs, and hepatotoxicity accounts for about 22 percent of these failures. Traditionally, a variety of strategies have been used to predict hepatotoxicity during preclinical development. These include incubating compounds with cultured hepatocytes to measure cytotoxicity or induction of the various isoforms comprising the drug metabolizing CYP enzymes. Biochemical enzyme assays, using purified CYP enzymes or crude liver microsome extracts, are used to determine the substrate activities of drug candidates and to profile their metabolic products using chromatographic methods.

Animal studies have also been widely used to predict human hepatotoxicity. In these studies, rats or mice are dosed with various concentrations of the test compound, and the animals are monitored for important serum markers such as serum albumin, prothrombin, bilirubin, AST, ALT, and alkaline phosphate at different time points. The animals are then sacrificed, and a full histopathological analysis of the liver, kidney, and other important organs and/or tissues is carried out.

More recently, gene expression studies have been used to predict hepatotoxicity. The RNA is isolated from cultured hepatocytes or liver sections from animals and analyzed using microarray technology. The advantages of this approach include faster turnaround times and less labor compared to animal pathology studies, and the method (as applied to cultured hepatocytes) requires a smaller amount of the experimental compound. Many industrial and academic groups are attempting to identify key genes that are expressed during a hepatotoxic response. The goal is to create a database that contains the gene expression patterns of known hepatotoxins and associated liver pathologies. The database is then used to predict the mechanism of hepatotoxicity by comparing the gene expression patterns of a new compound to those of reference compounds. This approach is still under development, and the number of marker genes reported to be relevant for the rat model varies from 400 to over 3000 genes. See "Serious liver injury: leading reasons for drug removals, restrictions" www.fda.gov/fdac/features/2001/301_liver.html; and ToxExpress™ Application Note, GeneExpress ToxExpress Predictive System™, Gene Logic, Gaithersburg, Md. (2002).

Unfortunately, none of the traditional approaches adequately predicts the hepatotoxic potential of drugs that reach the marketplace. At least three drugs within the last five years, Duract (bromfenac), Trovan (trovafloxacin) and Rezulin (troglitazone), have significant use limitations or were pulled from the market due to human hepatotoxicity. Thus, there is a great need for new methods to predict hepatotoxicity, and to use these methods early in the lead optimization process to save time and cost.

SUMMARY

The techniques of the present invention address the above need by providing methods, program instructions and apparatus that assess the toxicity of a stimulus. The invention accomplishes this by using imaging technologies to analyze the effects of a stimulus on hepatocytes or other cell types.

One aspect of the invention provides methods of assessing the hepatotoxicity of a stimulus, by performing the following operations: (a) exposing a hepatocyte culture to the stimulus; (b) imaging the hepatocytes; (c) analyzing an image of the hepatocytes to extract features characterizing the hepatocytes; and (d) classifying the stimulus by quantitatively evaluating the extracted features to identify one or more hepatotoxic pathologies resulting from the stimulus. Examples of hepatotoxic pathology classifications include necrosis, cholestasis, steatosis, fibrosis, apoptosis, and cirrhosis.

Another aspect of the invention provides methods of identifying a necrotic hepatotoxic pathology resulting from a stimulus. Such methods may be characterized by the following operations: (a) exposing a hepatocyte culture to the stimulus; (b) contacting the hepatocyte culture with markers relevant to necrosis (e.g., esterase activity and cell membrane permeability); (c) imaging the hepatocyte culture; (d) analyzing images of the hepactocyte culture to extract features relevant to necrosis; and (e) characterizing the necrotic response of the hepatocyte culture to the stimulus based on the extracted features. In one embodiment, the method identifies average levels of esterase activity and cell membrane permeability for the hepatocyte culture based on the extracted features. This information is then used to characterizing the necrotic response.

Still another aspect of the invention pertains to methods of identifying an apoptotic hepatotoxic pathology resulting from a stimulus. Such methods may be characterized by the following operations: (a) exposing a hepatocyte culture to the stimulus; (b) treating the hepatocyte culture under conditions that distinguish apoptotic and non-apoptotic hepatocytes (e.g., washing, exposing to markers for enzyme activity, exposure to markers for DNA); (c) imaging the hepatocyte culture; (d) analyzing images of the hepactocyte culture to extract features relevant to apoptosis; and (e) characterizing the apoptotic response of the hepatocyte culture to the stimulus based on the extracted features.

In a specific embodiment, the method includes (a) exposing a first and second hepatocyte culture to the stimulus; (b) performing a single step preparatory treatment of the first hepatocyte culture, wherein the single step preparatory treatment does not include washing; (c) performing a multi-step preparatory treatment of the second hepatocyte culture, wherein the multi-step preparatory treatment includes washing; (d) imaging the first and second hepatocyte cultures; (e) analyzing images of the first and second hepactocyte cultures to extract features relevant to apoptosis; and (f) characterizing the apoptotic response of the hepatocytes to the stimulus based on the extracted features. The method may use to the extracted features to, for example, identify condensation of the nuclei, cell adhesion, and average caspase-3 activity for the first and second hepatocyte cultures. This allows the method to characterize the apoptotic response of the first and second hepatocyte cultures to the stimulus based on the characteristics of the nuclei, cell adhesion, and average caspase-3 activity.

Yet another aspect of the invention pertains to computer program products including machine-readable media on which are stored program instructions for implementing a portion of or an entire method as described above. Any of the methods of this invention may be represented, in whole or in part, as program instructions that can be provided on such computer readable media. In addition, the invention pertains to various combinations of data generated and/or used as described herein. Examples include databases, data structures, and linked lists.

These and other features and advantages of the present invention will be described in more detail below with reference to the associated figures.

DETAILED DESCRIPTION OF A PREFERRED EMBODIMENT

I. Introduction and Overview

Figure 1A:
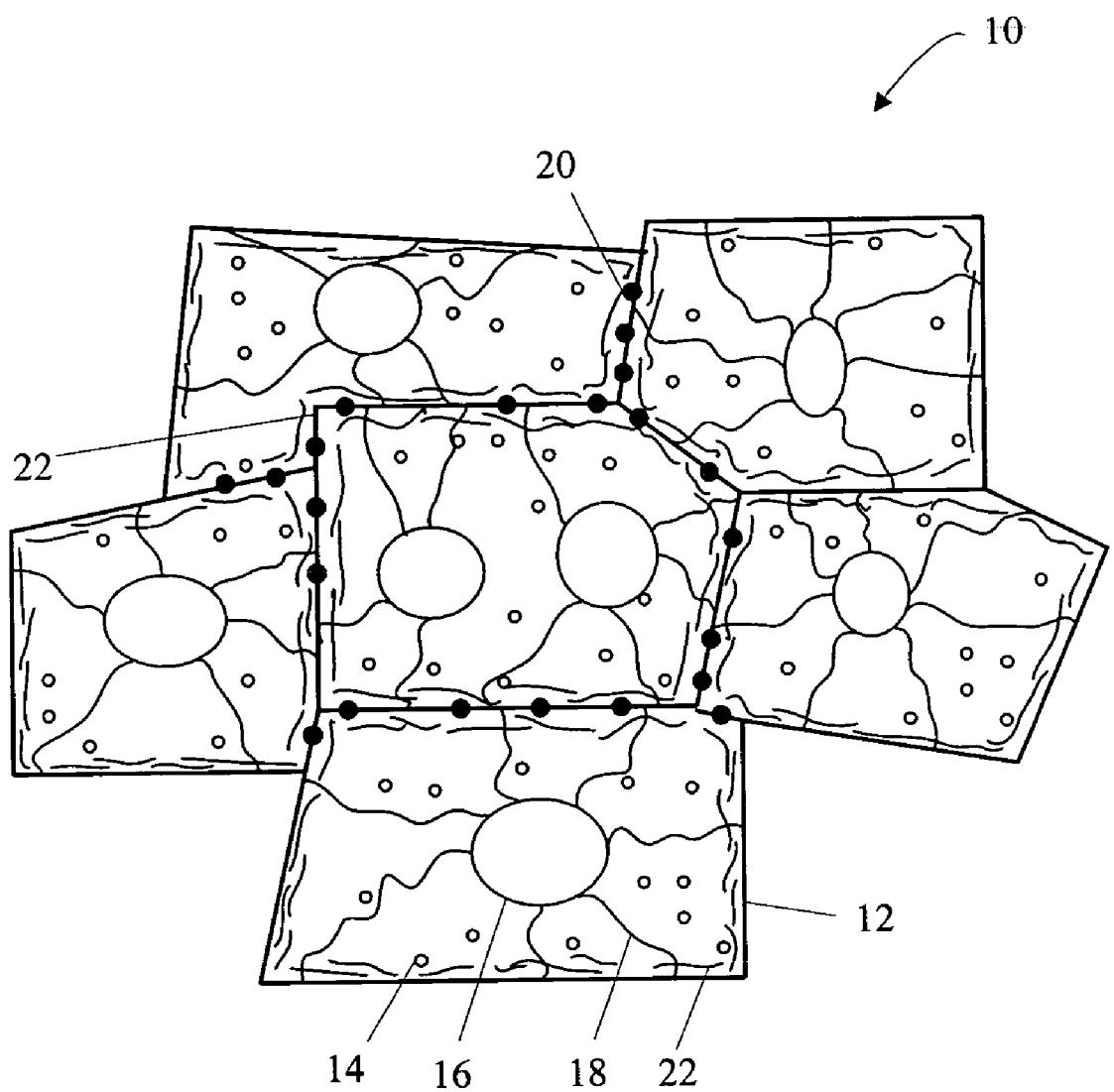
FIG. 1A is a cartoon representation of normal hepatocytes, showing various features as they might appear in the absence of a toxic response.

Hepatotoxicity is a major safety concern for drug development. As explained above, a variety of strategies traditionally have been used to predict hepatotoxicity during preclinical development. As indicated, the existing techniques have serious limitations and in fact some drugs have recently been banned or significantly limited in use due to late discovery of human hepatotoxicity. Accordingly, there is a need for better methods to predict human hepatotoxicity earlier in the drug development process.

This invention employs image and data analysis technology to provide an indication of whether a particular compound or other stimulus is hepatotoxic. Additionally, it may classify hepatotoxicity by the specific pathologies. This detailed classification can be beneficial for drug development in a number of ways.

First, knowing the exact pathology caused by a given compound can help to determine whether the compound should be abandoned as a drug candidate or whether it might be redesigned (e.g., subjected to a slight molecular change) to reduce its liabilities. If modification is likely to be successful, identification of the particular pathology elicited can also provide insight about which specific modifications are likely to reduce toxicity.

In addition, knowing the pathology associated with a given stimulus can help to determine the nature of the risk associated with the stimulus. In general, a stimulus that exhibits some level of cytotoxicity may or may not represent a low overall risk to a person's health. But knowing the particular pathology caused by a given stimulus can provide more specific information about the level of risk presented by the stimulus. For instance, some pathologies are only problematic or otherwise relevant when the condition to be treated is a chronic condition, e.g., fribrosis or cirrhosis of the liver. Other pathologies are only problematic for acute conditions, where the compound under investigation is administered over a relatively short period of time, possibly in high doses.

As explained further below, the invention extends to toxicity and pathologies in a wide range of systems (e.g., cell types, cell lines, tissues, etc.) other then hepatocyte systems. Examples include toxicity in dermal cells, kidney cells, neurons, etc. For convenience, the invention will be described primarily in terms of hepatotoxicity.

In accordance with this invention, toxicity may be detected by image and data analysis in various ways. Most conservatively, any effect to a cell that is not considered the principal action of the stimulus of interest is viewed as an, off-target effect, or effect is viewed as an indicator of potential toxicity. More specific assays consider particular indicia of toxicity or a particular pathology. One such assay considers increased level of cell necrosis in wells exposed to the stimulus in question. Other assays consider indicia of specific pathologies such as cholestasis or steatosis.

Regarding off-target effects, most stimuli, particularly those involving exposure to drug or drug candidates, are evaluated for their effect on a target (i.e., a protein or other component of the cell that is implicated in a disease pathway). "On-target" effects are those effects of the stimulus that arise from action on the target itself. In the context of this invention, these effects are manifest as phenotypic changes. Of course, other effects, unrelated to the effect of the stimulus on the target may also elicit phenotypic changes. The phenotypic differences between control and test cells are deemed to be "on-target" effects when these differences pertain to the presence or function of the target. For example, if a compound is being investigated for its ability to arrest mitosis, on-target effects include phenotypic manifestations of arrested mitosis. If an image analysis shows that an unnaturally high percentage of cells exposed to the particular drug have their nuclear DNA in the mitotic state, as opposed to an interphase state, then the drug may be deemed to have "on target" effects.

On the other hand, observed phenotypic differences between test and control cells are deemed "off-target" effects when they do not pertain to the presence or function of the target. For example, in the arrested mitosis target example, an observed deviation from control in the compactness of the cells' Golgi apparatus may be deemed an off-target effect.

Because off-target effects are not apparently tied to the desired effect on a target, they may be suspect. In a sense, they represent "side-effects." In a conservative view of drug discovery or other biochemical research endeavor, off-target effects may be viewed as indicia of toxicity. Of course, not all "side-effects" represent a toxic response. But in some cases, ideal drugs have only on-target effects. The use and relevance of off-target effects in biological investigations is described more fully in U.S. patent application Ser. No. 10/621,821, filed Jul. 16, 2003, naming Kutsyy as inventors, and titled "Methods and Apparatus for Investigating Side Effects," which is incorporated herein by reference for all purposes.

As explained elsewhere herein, indicia of hepatotoxicity or specific hepatic pathologies are provided by analyzing images of markers for the specific pathologies. Accordingly, the image analysis methods and apparatus of the present invention may classify stimuli according to a degree of hepatotoxicity and/or a particular pathology. As explained, drug-induced hepatotoxicity in humans or animals can be classified according to specific cellular morphologies of hepatic injury.

Most agents that are acutely toxic to the liver lead to cytotoxic or cholestatic injury. Necrosis and apoptosis are forms of such cytotoxicity. These conditions are manifest by specific and consistent phenotypic changes that can be detected by image analysis. Steatosis is another form of cytotoxicity. It is characterized by an accumulation of lipid containing vacuoles within hepatocytes, which can be detected by image analysis. Cholestasis is characterized by arrested bile flow and accumulation of bile pigment within the hepatic parenchyma. Aspects of cholestasis, such as modification of tight junctions between adjacent cells, can be detected by image analysis. Chronic injury caused by drug-induced hepatotoxicity can lead to hepatitis, fibrosis, and cirrhosis. Image-based methods of this invention can identify some or all of these liver conditions.

With reference to FIG. 1A, shown is a cartoon representation of a group of normal hepatocytes with various features as they might appear in the absence of a toxic response. The group of hepatocytes 10 includes individual hepatocytes 12 adjacent to each other, such that the individual hepatocytes contact each other to form roughly block shaped bodies (as opposed to smooth roughly circular shaped bodies). At the interfaces of individual hepatocytes 12, various tight junctions 20 can be present. These tight junctions provide pathways for inter-cellular transport between adjacent hepatocytes. It is believed that modification of tight junctions may implicated in cholestasis and possibly other toxic responses of hepatocytes.

A single hepatocyte cell 12 includes a nucleus 14, tubulin filaments 16, vacuoles 18, and various other organelles and features not shown in the present cartoon representation. The tubulin 16 is generally arranged as fibers that radiate from the nucleus 14 toward the periphery of the cell 12. The vacuoles 18 are small lipid-containing regions dispersed throughout the cytoplasm of cell 12. In addition, the cell includes actin filaments 22 concentrated at the edge of the cell appearing as dense actin cables that form a connected mesh works in the interior of cell. Note that one of the hepatocytes is shown with two nuclei. It has been found that as many as 30% or more of the healthy hepatocytes in a given culture may have two nuclei (also designated as binuleate cells).

Figure 1B:
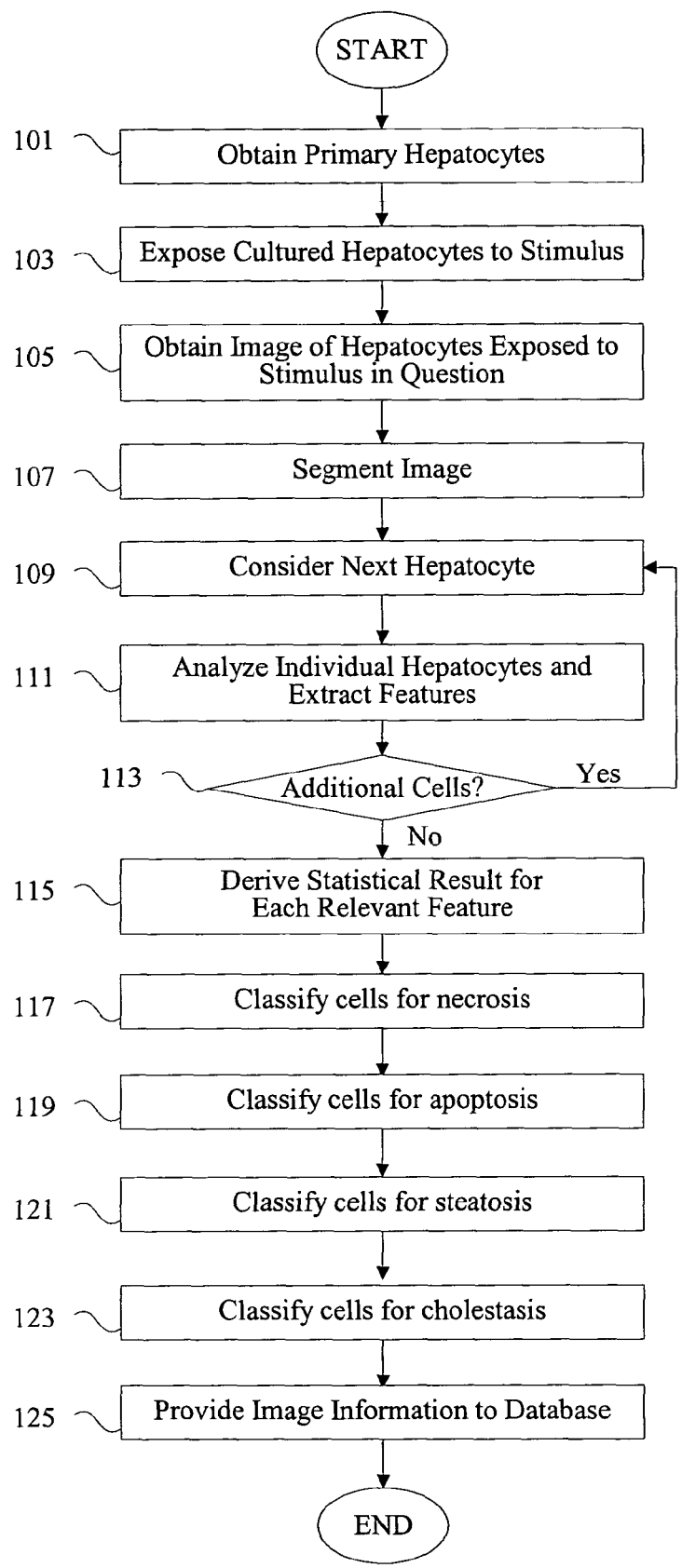
FIG. 1B is a flow chart depicting various operations commonly performed together in one implementation of a hepatotoxicity analysis of this invention.

In a process 100 depicted in FIG. 1B, hepatocytes exposed to a particular stimulus are imaged and then characterized by image analysis to provide information about hepatotoxicity. Understand that the process flow depicted in FIG. 1B is but one of many possible ways to implement the present invention. Other approaches will classify hepatocytes using different pathologies and/or different orders of operations to accomplish the same general result.

As depicted, the process 100 begins at block 101 where a culture of primary hepatocytes is obtained. These hepatocytes can be derived from rats, humans, or other species, and should give consistent responses when exposed to a given stimulus. The hepatocytes may be cultured in many different ways. Importantly, they should be cultured and presented in manner that illuminates their susceptibility to the particular stimulus under investigation and allows the salient features of their response to the captured in one or more images. Further discussion of the selection and culturing of primary hepatocytes for a hepatotoxicity assay and the support structures used to culture the primary hepatocytes is presented below in Section II: Culturing Hepatocytes for Assay.

Next, the process continues at a block 103 where the cultured hepatocytes are exposed to the stimulus under investigation. As explained above, many different stimuli can be tested in accordance with this invention. In a typical example, hepatocytes in multiple wells are contacted with a test compound. The compound may be provided at different concentrations in different wells. In at least one well, a control well, no compound is used. In another case, the multiple wells may be contacted with the compound for different lengths of time prior to fixing. These approaches allow a generation of a stimulus response path of the type described above. Each concentration or time point provides a different phenotypic point on the response path.

The next block in the depicted process (block 105) involves obtaining an image of the hepatocytes exposed to the stimulus under investigation. Single or multiple images are acquired from the same well. Frequently, multiple images will be taken at different "channels." Each such channel may be associated with a different marker, which highlights a specific feature of the cell such as a particular macromolecule or organelle. Each separate image provides a different piece of information that can be used to characterize the hepatocytes in culture.

In many embodiments, the individual cells of the image are separately analyzed, apart from the background in the image, to obtain statistical results that characterize the impact of the stimulus on various features of the cells. To this end, the image must be "segmented" to separate regions of the image associated with individual cells. Each "segment" of the image is a group of contiguous pixels associated with an individual cell. Block 107 in flow chart 101 indicates segmentation.

With the image segmented, image analysis logic can evaluate those pixels associated with various individual hepatocytes in order to extract particular features associated with an individual cell. In addition, the logic classifies individual hepatocytes by toxic effect, including individual pathologies.

In flow chart 100, the separate consideration of individual cells is depicted as a loop bracketed by blocks 109 through 113. In block 109, the process considers the "next" hepatocyte in the image. Note that, depending upon the processing capabilities of the image analysis system, multiple hepatocytes from the segmented image may be analyzed in parallel. Nevertheless, the analysis of each hepatocyte is a logically discrete operation; hence the loop in process 100.

Once a hepatocyte is chosen at block 109, then the chosen hepatocyte is analyzed and features are extracted from the image of the hepatocyte at block 111. For instance, specific cell features, which signal particular morphological, compositional, etc. aspects of the cell, can be extracted. These features may be associated with various cell components for which markers are provided. Examples of such components include Golgi, tubulin, actin, nuclear DNA, lipids, tight junctions, histones, activated caspase-3, and the like. Once features are extracted from the hepatocyte under consideration, then at 113, it is determined whether additional hepatocyte images remain to be analyzed. If so, then the process continues at 109. If not, then the process continues at block 115.

Once the relevant features are extracted from the individual hepatocyte images, then, at a block 115, the process derives a statistical result from among the cells in the image for each relevant feature in the hepatotoxicity study. The statistical result is used to characterize the impact of the stimulus on the relevant feature. The statistical result can be a mean value of a feature in question, an average value, a standard deviation, a variance, etc.

With the statistical results obtained for the set of hepatocytes, the depicted process next determines whether the hepatocytes exhibit necrosis (i.e., the stimulus induced necrosis). See decision 117. Next, the process may further classify the stimulus based upon whether apoptosis occurred. See block 119. In each case, the cells have died, possibly as a result of exposure to the stimulus under consideration.

Next, the statistical result is used to determine if the stimulus should be classified as inducing steatosis. See block 121. As explained elsewhere herein, steatosis is a pathology manifest by the accumulation of liquid containing vacuoles within the hepatocyte cytoplasm.

Next, the algorithm classifies the stimulus under consideration for cholestasis induction. As explained, cholestasis is characterized by arrested bile flow and accumulation of bile pigment within the hepatocyte. See block 123.

In alternative embodiments, alternative and/or additional classifications and analysis may be performed on the cell image under consideration. Some of these will be described elsewhere herein. Others will be apparent to those of skill in the art. Note that the order of the pathology analysis presented above is not important to the invention. The four pathologies can be considered in any order. Other pathologies can be considered before or after those depicted in the figure, or they may be interleaved with the pathologies in question.

When the cells have been classified according to pathology, the process may be considered complete. However, it is frequently desirable to provide image analysis information to a database that identifies the stimulus under consideration together with the image analysis information for individual hepatocytes and/or population statistics associated with all hepatocytes appearing in the image. See block 125.

Some of the terms used herein are not commonly used in the art. Other terms may have multiple meanings in the art. Therefore, the following definitions are provided as an aid to understanding the description herein. The invention as set forth in the claims should not necessarily be limited by these definitions.

The term "component" or "component of a cell" refers to a part of a cell having some interesting property that can be characterized by image analysis to derive biologically relevant information. General examples of cell components include biomolecules and subcellular organelles. Specific examples of biomolecules that could serve as cell components include proteins and peptides, lipids, polysaccharides, nucleic acids, etc. Sometimes, the relevant component will include a group of structurally or functionally related biomolecules. Alternatively, the component may represent a portion of a biomolecule such as a polysaccharide group on a protein, or a particular subsequence of a nucleic acid or protein. Collections of molecules such as micells can also serve as cellular components for use with this invention. And subcellular structures such as vesicles and organelles may also serve the purpose.

The term "marker" or "labeling agent" refers to materials that specifically bind to and label cell components. These markers or labeling agents should be detectable in an image of the relevant cells. Typically, a labeling agent emits a signal whose intensity is related to the concentration of the cell component to which the agent binds. Preferably, the signal intensity is directly proportional to the concentration of the underlying cell component. The location of the signal source (i.e., the position of the marker) should be detectable in an image of the relevant cells.

Preferably, the chosen marker binds specifically with its corresponding cellular component, regardless of location within the cell. Although in other embodiments, the chosen marker may bind to specific subsets of the component of interest (e.g., it binds only to sequences of DNA or regions of a chromosome). The marker should provide a strong contrast to other features in a given image. To this end, the marker should be luminescent, radioactive, fluorescent, etc. Various stains and compounds may serve this purpose. Examples of such compounds include fluorescently labeled antibodies to the cellular component of interest, fluorescent intercalators, and fluorescent lectins. The antibodies may be fluorescently labeled either directly or indirectly.

The term "stimulus" refers to something that may influence the biological condition of a cell. Often the term will be synonymous with "agent" or "manipulation." Stimuli may be materials, radiation (including all manner of electromagnetic and particle radiation), forces (including mechanical (e.g., gravitational), electrical, magnetic, and nuclear), fields, thermal energy, and the like. General examples of materials that may be used as stimuli include organic and inorganic chemical compounds, biological materials such as nucleic acids, carbohydrates, proteins and peptides, lipids, various infectious agents, mixtures of the foregoing, and the like. Other general examples of stimuli include non-ambient temperature, non-ambient pressure, acoustic energy, electromagnetic radiation of all frequencies, the lack of a particular material (e.g., the lack of oxygen as in ischemia), temporal factors, etc.

A particularly important class of stimuli is chemical compounds, including compounds that are drugs or drug candidates and compounds that are present in the environment. The biological impact, including toxicity, of chemical compounds is frequently manifest as clear phenotypic changes.

Specific examples of biological stimuli include exposure to drug candidate compounds, hormones, growth factors, antibodies, or extracellular matrix components. Or exposure to biologics such as infective materials such as viruses that may be naturally occurring viruses or viruses engineered to express exogenous genes at various levels. Biological stimuli could also include delivery of antisense polynucleotides by means such as gene transfection.

Other specific stimuli include exposure of cells to conditions that promote cell fusion. Specific physical stimuli could include exposing cells to shear stress under different rates of fluid flow, exposure of cells to different temperatures, exposure of cells to vacuum or positive pressure, or exposure of cells to sonication. Another stimulus includes applying centrifugal force. Other specific stimuli include changes in gravitational force, including sub-gravitation, application of a constant or pulsed electrical current. Still other stimuli include photobleaching, which in some embodiments may include prior addition of a substance that would specifically mark areas to be photobleached by subsequent light exposure. In addition, these types of stimuli may be varied as to time of exposure, or cells could be subjected to multiple stimuli in various combinations and orders of addition. Of course, the type of manipulation used depends upon the research endeavor at hand.

The term "phenotype" generally refers to the total appearance of an organism or cell from an organism. In the context of this invention, cellular phenotypes and their representations in processing systems (e.g., computers) are particularly interesting. The phenotypic characteristics of a cell are functions of the cell's genetic constitution and environment. Often a particular phenotype can be correlated or associated with a particular biological condition or mechanism of action resulting from exposure to a stimulus. Generally, cells undergoing a change in biological conditions will undergo a corresponding change in phenotype. Thus, cellular phenotypic data and characterizations may be exploited to deduce mechanisms of action and other aspects of cellular responses to various stimuli.

A selected collection of data and characterizations that represent a phenotype of a given cell or group of cells is sometimes referred to as a "quantitative cellular phenotype." This combination is also sometimes referred to as a phenotypic fingerprint or just "fingerprint." The multiple cellular attributes or features of the quantitative phenotype can be collectively stored and/or indexed, numerically or otherwise. The attributes are typically quantified in the context of specific cellular components or markers. Measured attributes useful for characterizing an associated phenotype include morphological descriptors (e.g., size, shape, and/or location of the organelle) and composition (e.g., concentration distribution of particular biomolecules within the organelle). Other attributes include changes in a migration pattern, a growth rate, cord formation, an extracellular matrix deposition, and even cell count. Often, the attributes represent the collective value of a feature over some or all cells in an image (e.g., some or all cells in a specific well of a plate). The collective value may be an average over all cells, a mean value, a maximum value, a minimum value or some other statistical representation of the values.

The quantitative phenotypes may themselves serve as individual points on "response curves." A phenotypic response to stimulus may be determined by exposing various cell lines to a stimulus of interest at various levels (e.g., doses of radiation or concentrations of a compound). In each level within this range, the phenotypic descriptors of interest are measured to generate quantitative phenotypes associated with levels of stimulus.

The term "path" or "response curve" refers to the characterization of a stimulus at various levels. For example, the path may characterize the effect of a chemical applied at various concentrations or the effect of electromagnetic radiation provided to cells at various levels of intensity or the effect of depriving a cell of various levels of a nutrient. Mathematically, the path is made up of multiple points, each at a different level of the stimulus. In accordance with this invention, each of these points (sometimes called signatures) is preferably a collection of parameters or characterizations describing some aspect of a cell or collection of cells. Typically, at least some of these parameters and/or characterizations are derived from images of the cells. In this regard, they represent quantitative phenotypes of the cells. In the sense that each point or signature in the path may contain more than one piece of information about a cell, the points may be viewed as arrays, vectors, matrices, etc. To the extent that the path connects points containing phenotypic information (separate quantitative phenotypes), the path itself may be viewed as a "concentration-independent phenotype." The generation and use of stimulus response paths are described in more detail in U.S. patent application Ser. No. 09/789,595, filed Feb. 20, 2001 naming Vaisberg et al., and titled, "CHARACTERIZING BIOLOGICAL STIMULI BY RESPONSE CURVES," and U.S. patent application Ser. No. 10/892,450 filed on the same day as the instant application, naming V. Kutsyy, D. Coleman, and E. Vaisberg as inventors, and titled, "Characterizing Biological Stimuli by Response Curves," both of which are incorporated herein by reference for all purposes.

As used herein, the term "feature" refers to a phenotypic property of a cell or population of cells. Typically, the points in a response curve of this invention are each comprised of multiple features. The terms "descriptor" and "attribute" may be used synonymously with "feature." Features derived from cell images include both the basic "features" extracted from a cell image and the "biological characterizations" (including biological classifications such as cell cycle states). The latter example of a feature is typically obtained from an algorithm that acts on a more basic feature. The basic features are typically morphological, concentration, and/or statistical values obtained by analyzing a cell image showing the positions and concentrations of one or more markers bound within the cells.

II. Culturing Hepatocytes for Assay

Hepatocyte cultures are used in assays designed to assess hepatotoxicity. Some are used as controls and others are exposed to one or more stimuli that may produce toxic responses in hepatocytes. As explained, the cultures are imaged and analyzed to identify features that may be affected by the stimuli tested. The features are analyzed in order to categorize the stimulus according to pathology (or simply toxicity), as will be described in more detail below.

Hepatocyte cultures may be derived from rats, humans or other species appropriate to the stimulus under investigation. Generally, hepatocytes used in different experiments should give consistent responses when exposed to the same assay conditions. Preferably, therefore, they come from a relatively homogeneous pool so that cells taken from one source respond similarly to cells taken from a different source. Laboratory rats, being relatively homogeneous genetically in comparison to most human groups, may provide a suitably consistent source of hepatocytes for assays of this invention. However, the effects of a stimulus on rat hepatocytes sometimes fail to adequately represent the effects seen on human hepatocytes. Hence, human hepatocytes may be necessary for some investigations.

Transformed or immortalized human hepatocyte cell lines can provide a genetically homogeneous source for many assays. One widely used transformed hepatocyte cell line is HepG2 available from the American Type Culture Center as HB 8065. Hep G2 is also available from Amphioxus Cell Technologies of Houston, Tex.

Unfortunately, immortalized cells do not always provide a completely realistic model of normal hepatocytes. In particular, although the hepatoma derived cell lines are easy to culture and maintain, they may not express the full complement of Cytochrome P450 metabolizing enzymes. One approach to this problem is to genetically modify the immortalized cells to mimic the expression pattern of a non-immortalized cell.

For non-immortalized or primary cells, one may use either freshly-isolated cells, which have been recently harvested, or cryopreserved cells. Several commercial vendors provide fresh or cryopreserved primary hepatocytes from human, rat, dog, and primate species. These vendors include Xenotech LLC of Lenexa, Tex.; Tissue Transformation Technologies of Edison, N.J.; In Vitro Technologies of Baltimore, Md.; Gentest (a BD Biosciences company) of Woburn, Mass.; and BD Biosciences. Transplant ready/fresh human hepatocytes are available from In Vitro Technologies and Tissue Transformation Technologies. Freshly isolated cells are normally used within 24 hrs after harvesting. For some experiments, it is possible to use them at 72 hrs after harvest.

Although non-immortalized cells generally present a better model for hepatoxicity in assays than their immortalized counterparts, immortalized cells are usually easier to use. As indicated, primary human hepatocytes have a finite shelf-life and exhibit significant genetic variation across samples. Accordingly, another approach to culturing hepatocytes for an assay can include isolating a highly differentiated hepatocyte cell line that retains the metabolic activity of primary hepatocytes but has been immortalized to allow easy cultivation in vitro. For a more detailed description of established techniques for preparing such cell lines, see Kobayashi, et al., "Prevention of acute liver failure in rats with reversibly immortalized human hepatocytes," Science, 287:1258-1262 (2000).

Hepatocyte cultures can be grown in or on various support structures. For instance, a bare plastic support that includes nutrients can be used to support a culture. Similarly, a glass surface can be used to support a culture. Other kinds of supports can include extra-cellular matrices such as collagen or Matrigel (available from BD Biosciences, San Jose, Calif.). Such structures can be provided in multiwell plates, such as 384-well assay plates. Cultures of primary hepatocytes generally grow well in three-dimensional lattice structures.

In some embodiments, hepatocytes can be cultured with associated cells to encourage the hepatocytes to behave naturally in an assay. For instance, hepatocytes can be co-cultured with stromal cells such as fibroblasts. Co-culturing hepatocytes and support cells in this manner may improve the predictive qualities of the assays in some contexts.

A discussion of co-culturing is provided in U.S. Published Patent Application No. US-2002-0160442-A1 of Elias (filed Dec. 18, 2000), which is incorporated herein by reference for all purposes. As explained there, two separate cell types are exposed to a stimulus suspected of producing a biological condition (e.g., a specific toxic pathology). The two different cell types are co-cultured or otherwise allowed to interact with one another before and during exposure to the agent. The images of the cells show how the stimulus separately affects each of the cell types. Specifically, the images show how the phenotype of each cell type changes (or does not change) upon exposure to the stimulus. In this regard, the concept of a phenotype encompasses visual indicators showing migration patterns, growth rates, extra-cellular matrix depositions, etc.

In the context of this invention, the cultures and supports described above are intended to provide in vitro models of in vivo hepatocyte functioning. For example, a three-dimensional co-culture of primary human liver stroma and parenchymal cells can be provided in vitro in a manner that mimics in vivo liver tissue function.

For some assays, such as the cholestasis assay, it may be appropriate to culture "polarized hepatocytes." Such culture can mimic features of the biliary tree, such as bile ducts, and thereby cause the hepatocytes to secrete bile into a "duct" (the exposed portion of the culture) and otherwise behave as if they were part the biliary tree. Because cholestasis is characterized by inhibition of bile flow, such culturing facilitates characterization of cholestasis.

An exemplary procedure for preparing hepatocyte cultures for use with assays of this invention will now be described. Specifically, the procedure involves the use of primary rat hepatocytes as follows:

Isolation and Culture of Primary Rat Hepatocytes

1. Adult Sprague-Dawley male rats (250-350 g) are anesthetized with Isoflurane to induce an anesthetic plane by inhalation.

2. An initial incision is made with surgical scissors to the ribcage, proximal to the pubis through the skin and muscle wall, with care taken to avoid cutting the diaphragm.

3. The intestines are then moved from the abdominal cavity to the animal's side. The portal vein and inferior vena cava (IVC) are exposed and two surgical sutures are loosely placed around the portal vein.

4. The IVC is injected with 0.3 cc heparin (1000 U/mL). The peristaltic pump is turned on and the flow rate is set to 1 mL/min using Liver Perfusion Medium warmed to 37° C. (available from Gibco BRL, Div. of Life Technologies Inc., Gaithersburg, Md., Catalog #17701).

5. The portal vein is cannulated and the portal vein sutures are tightened. With care taken to avoid introducing any air bubbles, the perfusion line is connected to the catheter.

6. The animal is euthanized by cutting the heart and diaphragm. The rate of the peristaltic pump is slowly brought to 16 mL/min and perfused for 15 minutes.

7. After 15 minutes, the perfusion media is switched to Liver Digest Medium (Gibco BRL, Div. of Life Technologies Inc., Gaithersburg, Md., Catalog #17703) at 37° C. and perfused for 15 minutes.

8. The liver is removed and placed in a 10 cm dish. Next, the liver is minced with small scissors and the contents are poured into a sterile flask with 50 mL of DMEM supplemented with 100 U Dnase I.

9. The flask is incubated at 37° C. for 20 minutes. The cells are strained through sterile 100 micron mesh nylon.

10. The contents are centrifuged for 5 minutes at 50 g. The supernatant is then removed and the pellet is resuspended in 10 mL DMEM.

11. The hepatocytes are purified in 45% Percoll and centrifuged at 80×g for 5 minutes. The supernatant is discarded and the pellet is resuspended in 5 mL DMEM medium.

12. The cells are counted by Trypan blue exclusion.

13. Fifty thousand cells/well are plated in a 96 flat well plate pre-coated with collagen I (available from BD Biosciences, San Jose, Calif.), and incubated at 37° C./5% CO2 in HCM (available from Clonetics Corp. (division of BioWhittaker), San Diego, Calif.) for two hours. After 2 hours, unattached cells and medium are replaced with 100 uL of fresh medium.

As appreciated by those of skill in the art, other procedures for preparing hepatocyte cultures can also be used within the scope of the present invention.

III. Imaging and Segmentation

As indicated, the phenotypic data characterizing stimuli is derived, at least in part, from images of hepatocytes exposed to particular combinations of stimulus type and stimulus level. See block 105 in FIG. 1B, for example. Various techniques for preparing and imaging appropriately treated cells are described in the following U.S. patent applications: Ser. No. 09/310,879 by Crompton et al., entitled A DATABASE METHOD FOR PREDICITIVE CELLULAR BIONINFORMATICS, filed on May 14, 1999; Ser. No. 09/311,996 by Crompton et al., entitled DATABASE SYSTEM INCLUDING COMPUTER FOR PREDICTIVE CELLULAR BIONINFORMATICS, filed on May 14, 1999; and Ser. No. 09/311,890 by Crompton et al., entitled A DATABASE SYSTEM FOR PREDICITIVE CELLULAR BION- INFORMATICS, filed on May 14, 1999, each of which are incorporated by reference herein for all purposes.

Generally the images used as the starting point for the methods of this invention are obtained from cells that have been specially treated and/or imaged under conditions that contrast the cell's marked components with other cellular components and the background of the image. Typically, the cells are fixed, optionally washed, and then treated with a material that binds to the components of interest and shows up in an image (i.e., the marker). Preferably, the chosen agent specifically binds to the cellular component of interest, but not to most other cellular biomolecules. In some cases, the cells are treated with the marker prior to fixation. This may be appropriate when, for example, the marker is used to distinguish live and dead cells.

In the case of cells treated with a fluorescent marker, a collection of such cells is illuminated with light at an excitation frequency. A detector is tuned to collect light at an emission frequency. The collected light is used to generate an image, which highlights regions of high marker concentration.

Additional operations may be performed prior to, during, or after the imaging operation (105) of FIG. 1B. For example, "quality control algorithms" may be employed to discard image data based on, for example, poor exposure, focus failures, foreign objects, and other imaging failures. Generally, problem images can be identified by abnormal intensities and/or spatial statistics.

In a specific embodiment, a correction algorithm may be applied prior to segmentation to correct for changing light conditions, positions of wells, etc. In one example, a noise reduction technique such as median filtering is employed. Then a correction for spatial differences in intensity may be employed. In one example, the spatial correction comprises a separate model for each image (or group of images). These models may be generated by separately summing or averaging all pixel values in the x-direction for each value of y and then separately summing or averaging all pixel values in the y direction for each value of x. In this manner, a parabolic set of correction values is generated for the image or images under consideration. Applying the correction values to the image adjusts for optical system non-linearities, mis-positioning of wells during imaging, etc.

Note that the quality of the images is dependent on cell plating, compound dilution, compound addition and imaging focusing. Failures in any these systems can be detected by a variety of methods. For example, cell plating could fail because of a clogged tip in a delivery pipette. Such failure can be identified by adding a fluorescent dye or bead to the cell suspension. The fluorescence of this dye or bead is chosen to be at a different channel (wavelength) than the markers used to image cellular components. Another potential failure could occur during compound delivery. To detect such failures, one can add a fluorescent dye or bead in the compound plate before compound dilution. The amount of fluorescent dye or bead is proportional to the amount of compound. Yet another potential problem occurs when the focus of the image acquisition system changes during imaging. To account for such spatial biases, one can employ control wells containing, for example, cells with no or neutral compounds interspersed throughout the plate. Still another problem results from foreign objects (e.g., small dust particles) in the well. This can be addressed with image segmentation and statistical outlier identification techniques. Both manual and automated methods can be used to eliminate bad images from analysis.

In order for the images to provide useful information about individual hepatocytes, the hepatocytes should be well spaced and distinguishable from one another. Otherwise, segmentation may be difficult or impossible. If cell clumping makes identification of individual hepatocytes difficult, the cells can be seeded at a lower density or different culturing conditions can be used.

Growing cells on a three-dimensional matrix such as collagen or Matrigel may also present some challenges for imaging. In particular, autofocusing can be difficult when cells are located in a three-dimensional structure. However, culturing conditions and automated microscopy capabilities can be adjusted to keep a sufficient number of cells within an accessible focal plane. Furthermore, the spatial resolution can be adjusted according to the degree of magnification necessary for a particular assay. Other conditions that can be modified according to the segmentation needs of a particular assay include the use of markers (e.g., DAPI for DNA) and the cell fixation procedures implemented. An example of an automated microscopy system suitable for use with this invention is the Image Express available from Axon Instruments or the Discovery 1 available from Universal Imaging and Molecular Devices.

The goal of segmentation is to allow feature extraction on a cell-by-cell basis. Segmentation identifies discrete regions of an image that include only those pixels where the components of a single cell are deemed to be present. Thus, each representation is a bounded collection of pixels, each providing associated features characterizing a single cell.

Segmentation can be accomplished in numerous ways. These include use of techniques that identify regions of high DNA concentration (presumed to be nuclear regions) and watershed algorithms. Typically nuclear DNA markers provide a strong signal and there is a high contrast in the image and an edge detection based segmentation process can be used. The segmentation process typically identifies edges where there is a sudden change in intensity of the cells in the image and then looks for closed connected edges in order to identify an object. In some cases, segmentation can be conducted on confluent or semiconfluent cultures.

In one approach to segmentation, the image analysis tool initially identifies the nucleus of each cell captured in the image under consideration. If images from different channels are well registered, the nuclei can be first identified in the DNA channel and then overlaid to the image under consideration. The segmentation algorithm defines a "ring region" around each nucleus. Generally, this step serves to define the perinuclear region. This region encompasses some or all of the cytoplasmic cell components in a normal interphase cell. The general method is described in U.S. Published Patent Application No. US-2002-0141631-A1, published Oct. 3, 2002, naming Vaisberg, Cong, and Wu as inventors, and titled "IMAGE ANALYSIS OF THE GOLGI COMPLEX," which is incorporated herein by reference for all purposes.

To identify bi-nuclear cells (and not treat each nuclei as the locus of different cell), one may employ nearest neighbor algorithms and other algorithms of the type described in U.S. patent application Ser. No. 10/615,116, filed Jul. 11, 2003, naming Coleman et al., and titled "METHODS AND APPARATUS FOR CHARACTERISING CELLS AND TREATMENTS," which is incorporated herein by reference for all purposes.

A watershed algorithm has been found to provide very good segmentation even in cultures containing many abutting hepatocytes or cells of other types. A suitable algorithm for this purpose is described in U.S. Published Patent Application No. US-2002-0154798-A1, published Oct. 24, 2002, naming Cong and Vaisberg as inventors and, titled "EXTRACTING SHAPE INFORMATION CONTAINED IN CELL IMAGES." which is incorporated herein by reference for all purposes. The watershed approach does a particularly good job of correctly illustrating the shape of cells identified during segmentation. In some embodiments, employs image data for a cell shape-indicative marker (for example, cytoskeletal components, (e.g., tubulin), one or more cytoplasmic proteins (for example lactate dehydrogenase or total cell protein), or membrane components (e.g., lipids or plasma membrane receptors)) in a watershed technique. Markers that detect proteins localized on the cell surface may work well in this technique. Examples include the tight junction proteins zonula occludens-1 (ZO-1), ZO-2, and ZO-3, which are found at the interface of fused hepatocytes and other cells. Other reagents for segmenting cells include succinimidyl esters of carboxytetramethyl-rhodamine (TAMRA, Molecular Probes). This reagent labels the primary amine groups of proteins and can be used to label any cell, including hepatocytes.

IV. Detecting Necrosis and Apoptosis

Acute liver failure can be associated with such necrosis and apoptosis. Both of these pathologies are a manifestation of cell death. Yet, they have distinct features that can be utilized in image analysis to characterize a cell as necrotic, apoptotic, or neither apoptotic nor necrotic.

To determine whether hepatocytes are necrotic, various features can be assayed. General indicators of necrosis include increased membrane permeability, decreased enzyme activity, diffuse Golgi distribution in interphase cells, dilated mitochondria morphology, and compromised metabolic activity of mitochondria.

In one embodiment, an assay tests the membrane permeability of the treated hepatocytes. Generally, cells with highly permeable membranes are deemed to be necrotic. Accordingly, a stain that is not permeable to the cell membrane of live cells can be introduced to a culture of treated hepatocytes before the hepatocytes are fixed for imaging. One example of a stain that can be used is ethidium bromide homodimer (available from Molecular Probes, Inc., Eugene, Oreg.). The material strongly binds to nucleic acids, yet is substantially impermeable to the cell membranes of live cells. It has been found ethidium bromide homodimer binds to the DNA of dead cells with an approximately 40-fold increase in fluorescence intensity. Other impermeable DNA stains (e.g., acridine orange, propidium ionide) or other impermeable cellular stains (e.g., trypan blue or rhodmine labeled phalloidin, which labels actin filaments) can also be used.

Examples of cell enzymes that can be used to generally identify necrotic cells include esterases. Biochemical assays include measuring ATP levels, or the reduction of a tetrazolium salt into a colored formazon product (MTS or MTT assay). In one embodiment, a live cell stain such as calcein AM (available from Molecular Probes, Inc., Eugene, Oreg.) can be introduced to a treated hepatocyte culture prior to fixing. Calcein AM is a non-fluorescent dye that is cell permeable. The dye becomes fluorescent after cleavage of its ester groups by cellular esterases. This requires cellular energy, and is therefore a good indicator of live cells having intact membranes and functional mitochondria with intact ATP production machinery. The dye can also be used to observe live cell morphologies such as membrane blebbing, which is an early indicator of apoptosis. Although calcein AM is bright in live cells, its fluorescence intensity decreases with time after the cells are fixed. Hence, in some embodiments, the hepatocytes may be imaged prior to fixing. In other embodiments, the cells are imaged relatively soon after fixing. In either case, strongly fluorescing cells are likely to be live and non-fluorescing cells are likely to be necrotic. Another example of a stain that can be used either before or after fixing is CMFDA (i.e., 5-chloromethylfluorescein diacetate), which provides a good indicator of live cells. Like calcein AM, it penetrates the cell membrane. In living cells with esterase activity, its acetate group is cleaved to produce a green fluorescent protein (excitation 485 nm, emission 520 nm), which is trapped inside the live cell.

Diffuse Golgi can be identified by imaging cells stained with a Golgi binding marker such as labeled Lens culinaris lectin (LC lectin) or antibodies to proteins enriched in the Golgi complex, such as gp130, [beta]COP. From imaged cells, the Golgi can be characterized by locating the region in a cell where the Golgi resides, and mathematically analyzing the region for peakedness, texture, amount of Golgi complex in the region, etc. As specific examples, the mathematical characterization of the Golgi complex include the kurtosis of intensity values obtained from the image, eigenvalues of a singular value decomposition of intensity values obtained from the image, and at least one of a mean and a standard deviation of intensity values obtained from the image. A suitable procedure for characterizing Golgi is described in U.S. Published Patent Application No. US-2002-0141631-A1, published Oct. 3, 2002, which was previously incorporated herein by reference.

In addition to determining whether cells are necrotic, a determination can be made about whether the cells are apoptotic. Apoptosis is a form of cell death and follows a specific biochemical cascade of events. Generally, apoptosis may be activated in cells by an intrinsic program of gene activations or by exposure to harmful stimuli. Apoptosis is characterized by a pathway that includes changes in certain membrane proteins, depolarization of the mitochondrial membrane, release of cytochrome C from mitochondria, activation of various caspase enzymes (caspase 3 is a major isoform involved in apoptosis), condensation, fragmentation and granularization of the nuclei, and breakdown of various nuclear and cellular proteins including actin, and microtubules. In addition, apoptotic cells tend to become loosely attached to their substrate and can removed easily. Various of these specific manifestations of apoptosis that can be identified by image analysis include exposure of phosphatidyl serines on membrane proteins, the migration of cytochrome c from the mitochondria into other regions of the cell, changes of mitochondrial membrane potential, activation of caspase 3, cleavage of caspase substrates (PARP, microtubule and actin), and condensation, fragmentation and granularization of the nuclei.

Figure 2:
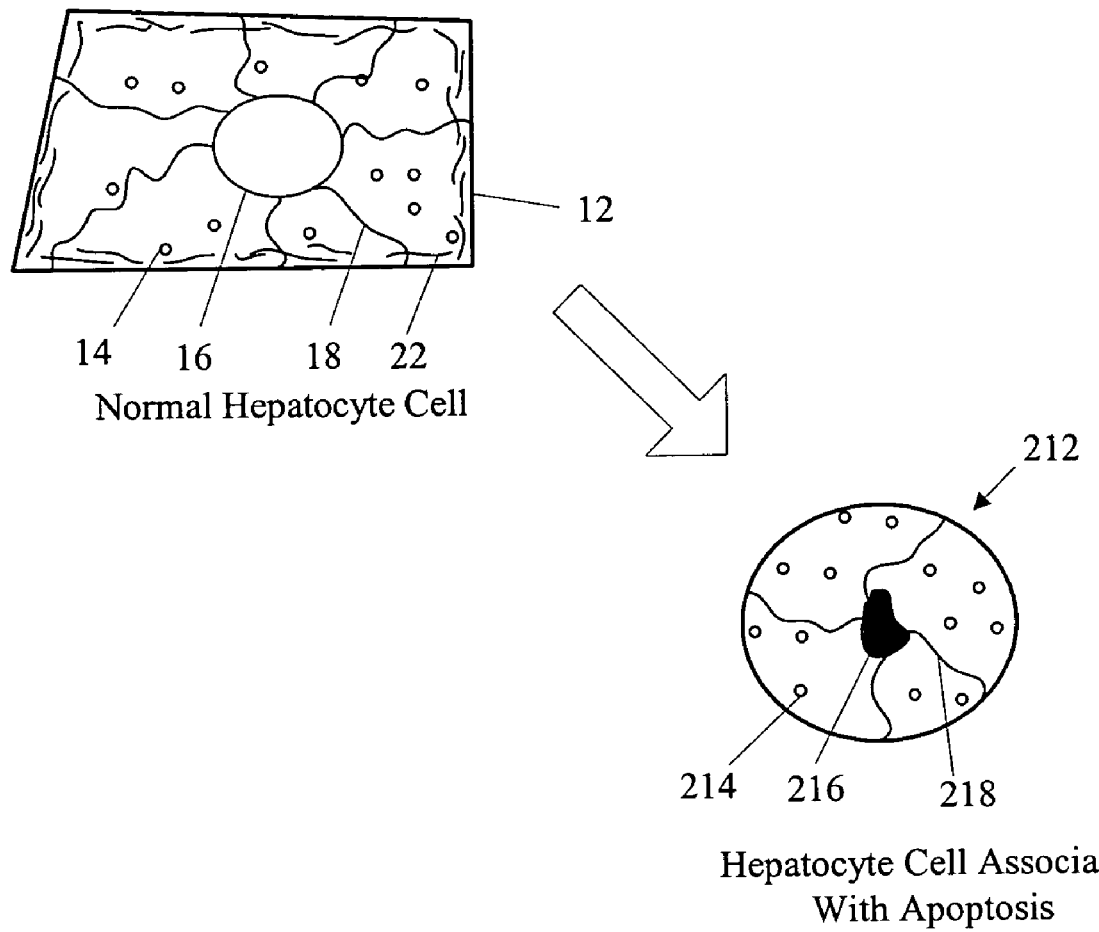
FIG. 2 is a diagrammatic representation of hepatocytes exhibiting drug-induced apoptosis.

FIG. 2 presents a cartoon depiction of a hepatocyte undergoing apoptosis in a hepatocyte 212. In comparison to a normal hepatocyte 12, the apoptotic cell has become smaller and more rounded. Furthermore, its nucleus 216 has condensed and become fragmented. Thus, markers for its nuclear components may exhibit brighter than normal signals. Furthermore, the tubulin fibers 218 appear less discrete as fiber bundles and more diffusely distributed throughout the cytoplasm. In contrast, the tubulin fibers 18 in a normal hepatocyte are disposed as thick tubulin bundles radially with respect to the nucleus 16 as shown.

Any one or more of the apoptosis features depicted in FIG. 2 or described elsewhere here may be employed to identify apoptotic cells in an image analysis procedure of this invention. A specific image-analysis algorithm for identifying necrotic and apoptotic hepatocytes is described below in the context of FIG. 3.

In one embodiment, annexin V is used to detect whether a cell is apoptotic. Annexin V is a commercially available marker from R&D Systems of Minneapolis, Minn. Annexin V is a member of a calcium and phospholipid binding family of proteins with vascular anticoagulant activity. Various synonyms for annexin V exist: placental protein 4 (PP4), placental anticoagulant protein I (PAP I), calphobindin I (CPB-I), calcium dependent phospholipid binding protein 33 (CaBP33), vascular anticoagulant protein alpha (VACa), anchorin CII, lipocortin-V, endonexin II, and thromboplastin inhibitor. Largely found on the cytosolic face of plasma membranes, this molecule has high affinity for phospholipids in the presence of physiological concentrations of calcium. See, Cookson, B. T. et al. (1994) Genomics 20:463; Grundmann, U. et al. (1988) Proc. Natl. Acad. Sci. USA 85:3708; and Huber, R. et al. (1992) J. Mol. Biol. 223:683, each of which is incorporated herein by reference.

During apoptosis, the proteins reverse orientation within the membrane to expose the phosphatidyl serine residues. Annexin V binds to the protein in this state. However, Annexin V does not bind to the protein when it is in its normal orientation. Accordingly, when annexin V binding is detected, the cell's death might be attributed to apoptosis. For purposes of an image analysis assay, a fluorescently labeled annexin V may be used.

In another approach, late-stage apoptosis can be detected by using dyes that are sensitive to changes in mitochondrial membrane potential, such as MitoTracker (available from Molecular Probes, Inc., Eugene, Oreg.). Normally, the mitochondrial membranes have a strong electrochemical gradient that drives ATP synthesis. During apoptosis, the mitochondria within a cell depolarize. Loss of mitochondrial membrane potential has been recognized as an early marker of apoptosis and is quantifiable by MitoTracker® Red.

In other embodiments, detection of cytochrome C outside of the mitochondria can be an indicator of apoptosis. Cytochrome C is required for respiration in the mitochondria, and detection of cytochrome C outside of the mitochondria indicates that the mitochondria have been compromised. More particularly, when the mitochondria stops functioning, the mitochondria releases cytochrome C. Green Fluorescent Protein (GFP) and/or antibodies also can be used to identify the presence of cytochrome C outside the mitochondria. See, e.g., Goldstein et al. (2000) Nature Cell Biol. 2:156; and Ogawa et al. (2002) Intl. J. Molecular Medicine 10:263.

In another embodiment, early-stage apoptosis can be detected by the presence of activated caspase 3, which is central to the apoptotic cascade. Different caspases may be activated, depending on the nature of the stimuli. Caspase 3, however, appears to be a key convergence point of most apoptotic pathways and its activation is an important hallmark of the apoptotic response. One method to detect caspase 3 activation is to use an antibody specific for activated caspase3 (Signaling Technology, Inc., Beverly, Mass.) in an immunoprecipitation experiment. In addition, there are modified substrates for caspase 3 that can be used in biochemical assays such as Asp-Glu-Val-Asp-AMC available from Molecular Probes, Inc., Eugene, Oreg.). Cleavage of the peptide by caspase 3 yields the blue fluorescent AMC product (7-amino-4-methyl coumarin). The same peptide substrate can be conjugated to rhodamine 110 (Molecular Probes) to yield a fluorescent product after cleavage by caspase 3. Another example is a FITC conjugated caspase3 inhibitor (caspTag, Serologicals, Norcross, Calif.), which recognizes and covalently link itself to the activated caspase3.

In yet another embodiment, specific labeling of fragmented DNA is used to determine whether the cell died by apoptosis. During apoptosis, enzymatic cleavage of the nuclear DNA occurs. This can be observed by a "TUNEL" assay that measures terminal transferase activity, which indicates the number of free ends of DNA generated by the degradation. An alternative to TUNEL is to use an antibody that recognizes Histone H2A.X phosphorylation (Upstate Cell Signaling, Waltham, Mass.) in response to DNA damage and strand breakage that occurs during apoptosis.

In addition, the effect on the nucleus can be observed by imaging the nucleus of a cell. In particular, the cell can be treated with a DNA stain (e.g., fluorescently labeled antibodies to DNA and fluorescent DNA intercalators such DAPI and Hoechst 33341 available from Molecular Probes, Inc. of Eugene, Oreg.) and then imaged to assess the cell based on the morphology of its nucleus. Apoptosis is often accompanied by condensation and fragmentation of the nucleus. Therefore indicia of apoptosis include relatively small nuclear regions of high signal intensity and "punctate" nuclear regions in which the nuclei separate into small points.

Note that condensed punctate nuclear regions are also found in mitotic cells. Thus, methods for characterizing mitosis may be used—in conjunction with other methods specific for apoptosis—to characterize the ability of a stimulus to induce apoptosis. "Mitotic index" is one measure of the mitotic state of cells. Generally, the mitotic index refers to the proportion of mitotic cells in the cell population. The cell cycle state (including the mitotic state) can be determined by various techniques such as those described in U.S. patent application Ser. No. 09/729,754, filed Dec. 4, 2000, naming Vaisberg et al., and titled "CLASSIFYING CELLS BASED ON INFORMATION CONTAINED IN CELL IMAGES," which is incorporated herein by reference for all purposes. In one approach, the mitotic index is determined from the intensity of the DNA signal in cells (mitotic cells have twice as much DNA as G1 cells) and the variance in the DNA signal intensity (greater variance suggests mitosis).

Another property of cells undergoing apoptosis is that they tend to become loosely attached to the substrate. Both cytoplasm shrinkage and loss of attachment is probably a result of cytoskeleton damage by caspases. This property can be detected by exposing the culture to a treatment that will tend to dislodge and remove loosely attached cells. One way to accomplish this is by carefully washing a cell culture under consideration. The level of apoptosis has been found to correlate well to a "washout coefficient" based on cell counts in washed and unwashed cultures exposed to a stimulus suspected of inducing apoptosis; e.g., (cc (unwashed)—cc(washed))/cc(unwashed).

It has been found that hepatocytes, cultured on a collagen substratum surface, stained using standard immunocytochemistry procedures, and washed using phosphate-buffered saline or Tris-buffered saline give washout coefficients that correlate strongly with apoptosis. For example, it has been found that approximately 40% or higher percentage of the cells exposed to a strong apoptosis inducing stimulus become dislodged during washing. Generally, large values of the coefficient indicate that the associated stimulus is a strong inducer of apoptosis.

Aside from washing the culture, centrifugation, shear force, mixing, and the like also can be used to dislodge apoptotic cells and provide classifying information corresponding to washouts.

In some embodiments, apoptosis can be analyzed using time-lapse imaging technology. As described above, an apoptotic event is characterized by condensation of the nuclei. A specific example of a time-lapse apoptosis experiment will now be described. Using multi-site time-lapse imaging of live cells expressing a GFP-histone2B (or any other GFP-tagged protein that functionally co-localizes with DNA) at low (5x-10x) magnification, the apoptotic event can be observed. Cells can be kept alive in their preferred environment using an environmental chamber with heat and carbon dioxide. Many wells can be sequentially visited and images can be taken. This process can be repeated every 10-15 minutes over a course of days in the presence of a compound or control, until hundreds of images are collected that can be collated into movies and analyzed qualitatively or quantitatively. Three structural pathways that the cells can take to an apoptotic death include the following.

First, some of the more traditional apoptotic inducers (e.g., Staurosporine, Tpen) cause cells to apoptose from interphase (G1, S, or G2). This can be visualized as condensation of the nuclei into a single small and bright condensed fragment.

Second, compounds that cause mitotic arrest (e.g., Taxol) cause cells to apoptose from mitotic (or arrested mitosis as the case may be). Cells that apoptose from this state result in a large array of multiple small DNA fragments. This may be a form of mitotic catastrophe.

Third, cells that are arrested in mitosis for a long period of time (e.g., with Taxol) may also decondense their DNA and become live, albeit, multinuclear cells. These cells will proceed to apoptose with a large array of multiple small DNA fragments.

The apoptotic states induced by second and third pathways above are sensitive to perturbations in the liquid layer, such that the cells are disturbed even in a "homogenous" assay by the addition of stain, without washing. The apoptotic state induced by first pathway is also easily washed away, but less easily than with the second and third pathways.

Using multi-site time-lapse techniques as described, apoptotic events can be quantified on a cell-by-cell basis over time to extract kinetic information.

Figure 3:
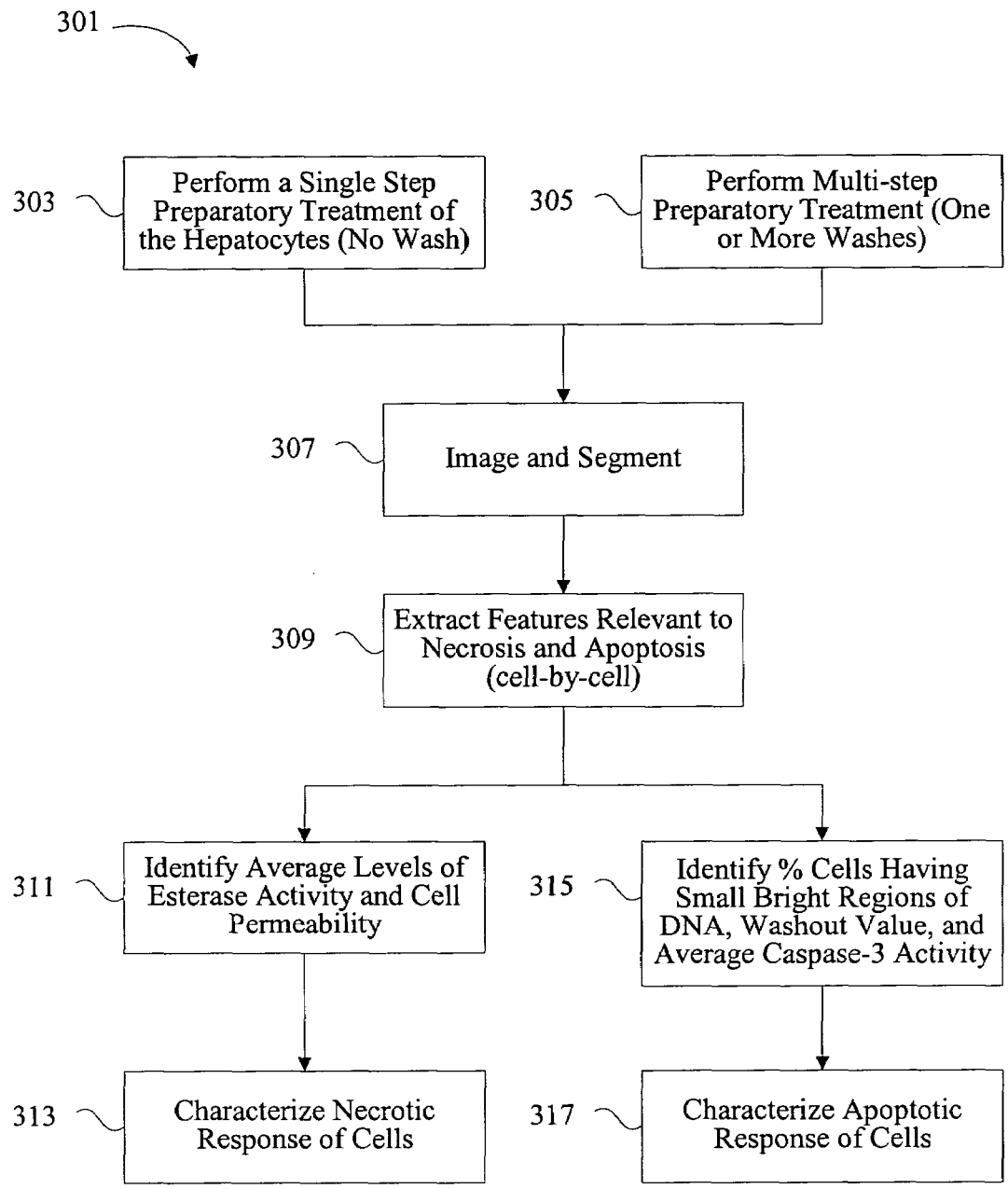
FIG. 3 is a flow chart depicting various operations commonly performed together in one implementation of a hepatotoxicity analysis configured to classify cells as apoptotic or necrotic.

FIG. 3 presents a flow chart highlighting some operations that may be used in an assay for apoptosis and necrosis in accordance with an embodiment of this invention. A depicted process 301 begins after the hepatocytes in two or more samples (e.g., hepatocyte cultures in separate wells of a plate) have been exposed to a stimulus as indicated at block 103 of FIG. 1B. Generally, the exact same stimulus is provided to the two or more hepatocyte samples. Then each of them is subject to a different set of preparatory treatments.

Importantly, one sample is washed and the other is not. Optionally, the samples are treated with different markers. As illustrated in a block 303, one hepatocyte sample is treated in a single step that does not include a wash step. In one specific embodiment, this step involves contacting the hepatocytes with a fixing agent, an esterase activity marker such as calcein AM, a cell membrane impermeable marker such as ethidium bromide homodimer, and a DNA intercalating stain such as Hoechst.

A second sample is subjected to a multi-step preparatory treatment 305 that includes one or more washes. One example of a multi-step preparatory treatment is a quadstain. This allows comparison of washed and unwashed samples to assess the stimulus' impact on cell adhesion. In one embodiment, the treatment includes contact with a tubulin marker (e.g., DM1-α), an actin marker (e.g, fluorescently labeled phalloidin), a DNA marker, a caspase-3 activity marker. In a specific example, the treatment includes the following sequence:

Cell plates are split into two groups: a one-step group and a quad-stain group. For the one step group, calceinAM and ethidium homodimer are added to the wells and the plates incubated for 30 min at 37 degrees. A fixative (4% paraformaldehyde, 5 ug/ml Hoechst 33342 in phosphate buffered saline) is added to each well and the plates are imaged. The following steps are used to treat wells in the quad-stain group (1) fixative, (2) wash buffer (e.g. phosphate buffered saline) (3) blocking buffer (Technova, catalog #T1682) (4) antibody cocktail with markers (Hoechst 3341, caspase3 antibody, rhodamine labeled DM1-α, and fluorescently labeled phalloidin), (5) wash, (6) incubation with a fluorescent secondary antibody to the caspase primary antibody, (7) wash, and (8) image. Hoechst 3341 is a DNA marker, caspase 3 is an apoptosis marker, DM1-α is a microtubule marker, and phalloidin is an actin marker.

After the hepatocyte samples have been separately treated as described (operations 303 and 305), they are imaged and segmented as indicated at block 307. This corresponds to operations 105 and 107 of FIG. 1B. Next, the images are separately analyzed to extract pertinent features on a cell-by-cell basis. See block 309. This corresponds generally to operations 109, 111, and 113 of FIG. 1B. From this point, the flow chart branches to analyze the images for apoptosis (one branch) and necrosis (a second branch). The analysis employs features extracted from both samples (the one receiving treatment 303 and the other receiving treatment 305).

On the necrosis branch, the method identifies average levels of esterase activity (e.g., calcein AM activity) and cell permeability (e.g., ethidium bromide homodimer binding) in cells of the image. See block 311. This operation represents a specific version of the "derive statistical result for each relevant feature" operation of FIG. 1B (block 115). From this information, the method characterizes the necrotic response of the hepatocytes. See block 313. In a specific embodiment, necrotic cells have low esterase activity and high cell permeability, while live cells have high esterase activity and low cell permeability. These features are obtained as statistical parameters across all cells in the image.

On the apoptosis branch, the method considers the condensation and/or fragmentation of the nuclei (using mitotic index for example), cell adhesion (using a washout coefficient for example), and average caspase-3 activity (or the activity of some other apoptosis marker). See block 315. As with operation 311 on the necrosis branch, operation 315 represents a specific embodiment of operation 115 from FIG. 1B. After the information relevant to apoptosis has been identified and considered, the method characterizes the apoptotic effect of the stimulus. See block 317. As discussed above, apoptosis is characterized by a lowering of cell adhesion, condensation of the nuclei, and increased caspase 3 activity—among other effects.

Note that the above assay method is but one of many apoptosis and/or necrosis assays within the scope of this invention. Various combinations of markers and features can be employed in image analysis techniques to assess the effects of stimuli on hepatocytes.

Another assay for apoptosis has been applied to cancer cells. And it should be generally applicable to other cell types as well. In the assay, cells exposed to a stimulus are divided into two samples. The first group is treated very simply; it is fixed and contacted with a DNA marker in a single step. In other words, it is treated with a cocktail containing only a fixative agent and a DNA marker (e.g., the Hoechst 33341 marker). Thereafter it is imaged without first washing. The second sample is subjected to a more elaborate procedure. The following sequence is employed: (1) fixed, (2) washed, (3) blocked, (4) cocktail with markers (e.g., Hoechst 3341, LC-lectin, DM1-α, and a primary antibody to the phosphorylated histone (pH3)), (5) wash, (6) contact with a fluorescent secondary antibody to the pH3 primary antibody, (7) wash, and (8) image. Hoechst 3341 is a DNA marker, LC-lectin is a Golgi marker, and DM1-α is a tubulin marker.

As indicated, one can use the washout coefficient in determining a level of apoptosis. Another indicator of apoptosis is a combination of (1) and a high mitotic percentage of cells with condensed DNA (using a DNA marker) and (2) a low mitotic index using a phospho-histone marker (e.g., a pH3 marker). As indicated, during apoptosis, the nuclear DNA becomes condensed and fragmented. Thus, proportion of cells with condensed DNA will increase. Of course, a stimulus that produces mitotic arrest will also give a high mitotic index using a DNA marker. So, a mere quantification of cells with condensed DNA using a DNA marker will not provide strong evidence of apoptosis. To more clearly distinguish stimuli that induce mitotic arrest from stimuli that induce apoptosis, the procedure uses a marker (e.g., an antibody) for a phosphorylated histone, e.g., phospho-histone 3 (pH3). During mitosis, the histones in the nucleus become phosphorylated. Therefore, mitotic index is measured using a pH3 marker will also give a high reading for the stimuli that induce mitotic arrest. However, during apoptosis, histones are not phosphorylated to such a degree. Therefore, a histone-based mitotic index will not be so high for apoptotic cells. One view of this distinction may be understood with reference to the following table.

|  | Cells with Condensed DNA | Mitotic Index (Histone) |
|---|---|---|
| Mitotic Arrest | High + | High + |
| Apoptosis | High + | Low − |

V. Detecting Steatosis

Figure 4A:
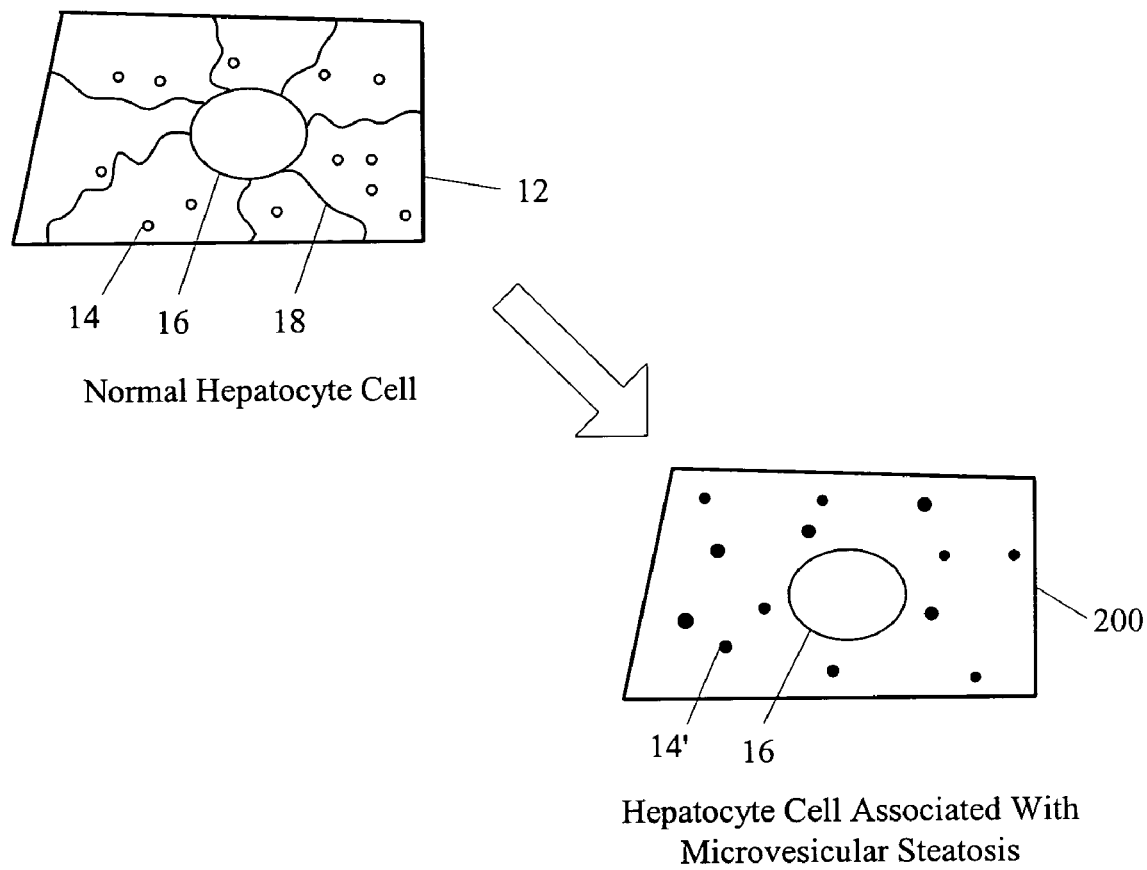
FIG. 4A is a diagrammatic representation of hepatocytes exhibiting microvesicular steatosis.
Figure 4B:
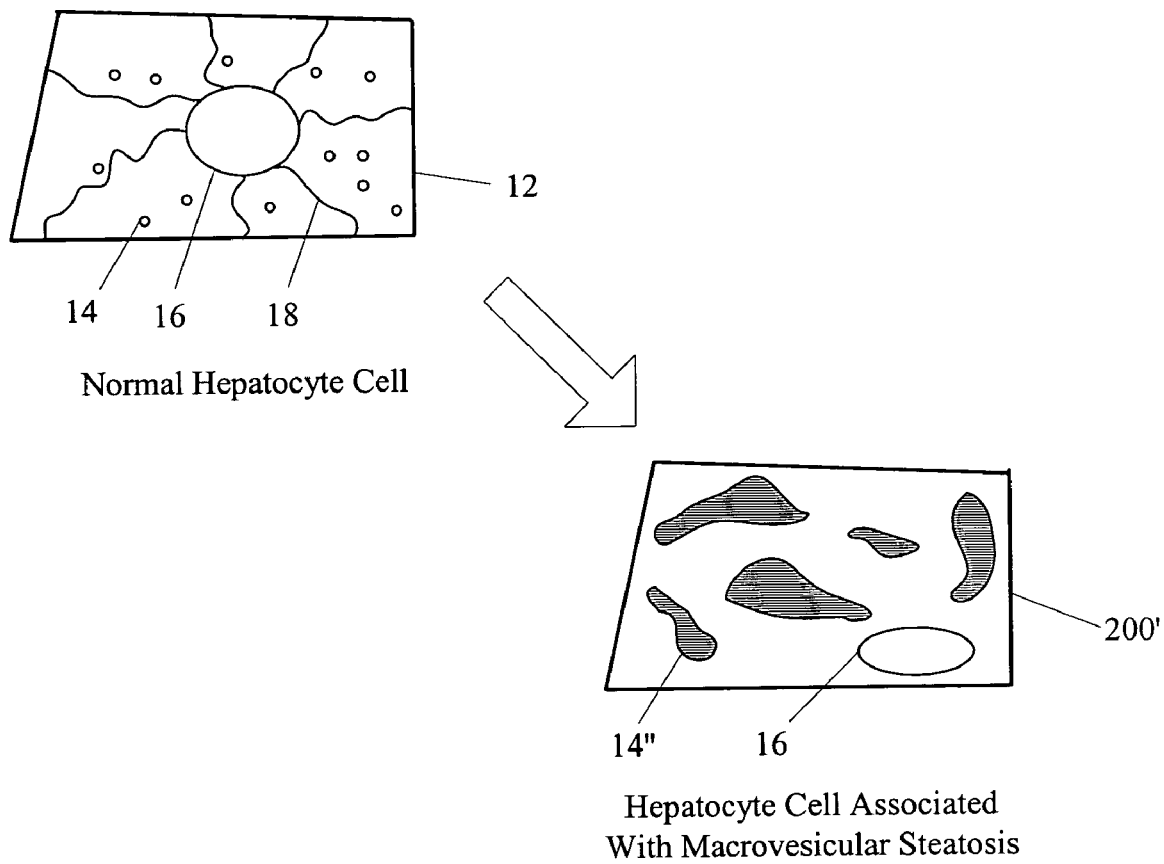
FIG. 4B is a diagrammatic representation of hepatocytes exhibiting macrovesicular steatosis.

FIGS. 4A and 4B present cartoon representations of hepatocytes associated with steatosis. Steatosis is a form of cytotoxicity characterized by a build up of triglycerides within hepatocytes. It is also manifest by an accumulation of lipid containing vacuoles 14 within the hepatocyte cells 200. It is caused by inhibition of lipid transport away from the liver or by inhibition of mitochondrial oxidation of fatty acids that normally participates in lipid breakdown. Accordingly, one way to determine that a cell exhibits steatosis includes detecting the buildup of lipids in the cell.

Steatosis can be microvesicular or macrovesicular. FIG. 4A shows a cartoon representation of microvesicular steatosis. As shown, the microvesicles 14' of hepatocyte 200 become more numerous than in the normal hepatocyte 12. In microvesicular steatosis, the numerous tiny lipid droplets do not displace the nucleus 16. FIG. 4B shows a cartoon representation of macrovesicular steatosis. Macrovesicular steatosis occurs when larger lipid droplets 14" are formed within hepatocyte 200' and displace the nucleus 16 to the periphery.

In one embodiment, lipid-binding markers are employed to detect steatosis. In a specific example, the lipid-binding fluorescent probe, Nile Red (available from Molecular Probes, Inc., Eugene, Oreg.) is introduced to in vitro cultures of hepatocytes exposed to a stimulus. Once the Nile Red has been introduced to the hepatocytes, the hepatocytes can be imaged. If a relatively large fluorescence signal is detected from the images, then it can be inferred that the hepatocytes may exhibit steatosis. In previous studies using the human hepatoma cell line HepG2, increased Nile Red binding was observed after the HepG2 cells were incubated with compounds known to cause hepatic fat accumulation in vivo, including estrogen, ethionine, cyclosporin A, and valproic acid. Image analysis can provide an indication of the locations, sizes, and shapes of lipid vesicles within hepatocytes to provide an additional indication of steatosis and whether it is microvesicular or macrovesicular.

An exemplary procedure for performing a Nile Red assay will now be described. Nile Red (Molecular Probes, Inc., Eugene, Oreg.) is diluted to 1:1000 in DMSO from a 1 mM stock solution and added to hepatocytes. The hepatocytes are then incubated for 2 hours in the dark. The hepatocyte cells are then washed two times in PBS and fixed in 3.7% formaldehyde with 1 uM Hoechst and incubated for 1 hour in the dark. Plates are washed 3 times with PBS and images are collected. As appreciated by those of skill in the art, modifications can be made to the assay within the scope of the present invention. Furthermore, alternative or additional assays can be used.

Alcohol, a common cause of steatosis, is a hepatotoxin that interferes with mitochondrial and microsomal function in hepatocytes, which leads to an accumulation of lipid. Also, the major toxic metabolite of alcohol, acetaldehyde, has been shown to impair microtubule polymerization and hepatic protein secretion. Thus, visualization of microtubule morphology using, for example, DM1-α as a marker may provide a useful assay for predicting hepatotoxicity caused by alcohol.

VI. Detecting Cholestasis

Generally, cholestasis is characterized as inhibition of bile flow caused by a wide variety of mechanisms that involve elements of the biliary tree, including bile ducts, ductules, the basolateral or canalicular membrane, the tight junctions or pericanalicular network of the hepatocytes, the ATPase, and transporters of the hepatocytes' basolateral and canalicular plasma membranes. It may involve defects of the transport of bile acids from the sinusoidal blood into hepatocytes or from hepatocytes into bile. Thus, assays for cholestasis include imaging of bile using light microscopy to directly measure the impairment of bile flow.

Some drugs may cause cholestasis by damaging pericanalicular microfilaments. For example, cytochalasin B has been shown to produce a prompt arrest of bile flow in rats, thereby resulting in cholestatic injury. In addition, phalloidin causes an increase in filamentous F actin around canaliculi and tight junctions. Thus, changes in actin morphology may be indicative of cholestatic injury.

Further, cholestasis has been implicated in the disruption of tight junction proteins. Hence, a method that images tight junctions can provide insight into the cholestasis-inducing effects of a given stimulus. One class of tight junction proteins that have been considered for this purpose is the zonula occludens-1 (ZO-1), ZO-2, and ZO-3. Other tight junction protein classes include claudin 1, 2, 3, and occludin. Fluorescent antibodies to ZO-1 can be used in cholestasis assays of this invention.

VII. Creating Models for Hepatotoxicity

Models for hepatotoxicity can be generated using a variety of methodologies known to those of skill in the art. U.S. patent application Ser. No. 10/892,450—"Characterizing Biological Stimuli by Response Curves," filed on the same day as the instance application), previously incorporated by reference, describes one such technique. It identifies relevant features and other parameters for image analysis classification models by analyzing stimulus response paths for various known toxins or other stimuli. The response paths and known mechanisms of action (or pathologies) comprise a training set for the model. Various potential models are compared based on their ability to correctly classify members of the training set. The classification is accomplished using distance measurements between the various stimulus response paths in a multi-dimensional feature space. Similar methods may be employed to generate hepatotoxicity models in accordance with this invention.

Generally, the training set includes signatures or response paths or signatures for diverse stimuli that have been previously classified by a trustworthy method. For example, the response paths may be obtained for stimuli having known toxicity (e.g., cholestasis, steatosis, necrosis, apoptosis, control, etc.). As explained above, the response paths are comprised of (or derived from) signatures of the stimuli at various levels or various times.

In one example of a training set, toxins A-F are known to induce cholestasis, toxins G-K are known to induce steatosis, toxins L-P are known to induce apoptosis in hepatocytes, compounds Q-T are known to be benign to hepatocytes, etc. Hepatocyte cultures are exposed to each of these toxins/compounds and imaged using a defined marker set and treatment regimen. Features extracted from the images comprise the training set for developing a hepatotoxicity model. The training set preferably includes some negative controls. These may be derived from stimuli that do not affect hepatocytes. They may also be derived from cell lines that are relatively insensitive to particular toxins, in comparison to hepatocytes. Further, the training set may include images of cells undergoing toxic responses other than hepatotoxicity. Examples include cardiotoxicity and neural toxicity.

The process of creating a model may identify specific features that are particularly useful in classifying hepatocyte pathologies. The raw training set will include a large number of features extracted from many images collected from different experimental conditions: i.e. cell types, compound concentrations, marker sets, etc. Multiple features from each image will be combined to produce a "signature," a large multidimensional vector comprised of values for each biological feature that might potentially be employed in the model. So, in other words, the initial data set (from the training set members) occupies a highly multidimensional space defined by all available biological features. At the end of the process, only some of these features (a subset) will be selected for the hepatotoxicity model. Obviously, there will be a vast number of possible subset combinations. The model generating process chooses a combination (feature subset) that does a good job of distinguishing between the various pathologies.

The various members of the training set (as represented by the respective signatures or response curves) can be grouped or classified based on distances in feature space. Various classification algorithms may be employed. Some are presented in "The Elements of Statistical Learning, Data Mining, Inference and Prediction," T. Hastie, R. Tibishirani, J. Freidman Springer 2001, which is incorporated herein by reference for all purposes. Examples include Nearest Neighbor methods, Linear Discriminant Analysis, and the like. If the training set is known to contain stimuli that produce eight different hepatocyte pathologies, for example, the classification algorithm may be asked to segregate the response curves into eight different groups (for the current model under consideration). The accuracy of this grouping is then assessed by comparing the grouping to the known pathologies (or other classifications) for the training set members. Good models will have relatively few misclassifications.

Note that models can be validated. Various validation techniques are known to those of skill in the art. Some of these employ test sets that do not overlap with the training set but have known classifications according to criteria such as mechanism of action, and the like. Others employ a "leave one out" technique in which the model is generated from all members of the training set, except one. The resulting model is then evaluated on the basis of its ability to properly classify the "left out" member. This process can be repeated numerous times by choosing different training set members to "leave out" during the model generating operation.

With relevant feature set identified, the model may be essentially complete. To use the model one extracts the relevant features from an image of hepatocytes treated with a stimulus having unknown toxicity. Then one measures distances between these features and features obtained from other stimuli having known toxic responses. Classification is based on distance (in feature space) between the features of the test stimuli and features of the various pre-classified stimuli. Alternatively, one can use a regression technique, a neural network, a support vector machine, etc. To develop an expression or analytical tool that takes feature values as input values and calculates a classification (pathology).

VIII. Database

According to various embodiments, a database is employed to assist in characterizing the toxic response of various stimuli or classes of stimuli. Preferably, the database is continuously monitored for quality by testing its ability to predict the hepatotoxicity of new compounds in animals and humans. In some embodiments, the database includes pathology data from other tissues, such as kidney tissue.

In other embodiments, it is appropriate to diversify the data sets by incorporating other assay technologies. For example, gene expression data using RNA isolated from in vitro hepatocyte cultures or animal liver biopsies can be useful for predicting specific mechanisms of toxicity that are difficult to detect using cell-based imaging approaches. In addition, new biomarkers can be identified from the gene expression data. These biomarkers may be useful in the cell imaging assays described above. For example, the gene products identified from genes specific to a steatosis response could be used to generate antibody reagents for the cell imaging assays. These antibody reagents can be used as novel diagnostic regions to monitor the serum levels of patients during clinical trials for early signs of hepatotoxicity.

VIII. Software/Hardware

Generally, embodiments of the present invention employ various processes involving data stored in or transferred through one or more computer systems. Embodiments of the present invention also relate to an apparatus for performing these operations. This apparatus may be specially constructed for the required purposes, or it may be a general-purpose computer selectively activated or reconfigured by a computer program and/or data structure stored in the computer. The processes presented herein are not inherently related to any particular computer or other apparatus. In particular, various general-purpose machines may be used with programs written in accordance with the teachings herein, or it may be more convenient to construct a more specialized apparatus to perform the required method steps. A particular structure for a variety of these machines will appear from the description given below.

In addition, embodiments of the present invention relate to computer readable media or computer program products that include program instructions and/or data (including data structures) for performing various computer-implemented operations. Examples of computer-readable media include, but are not limited to, magnetic media such as hard disks, floppy disks, and magnetic tape; optical media such as CD-ROM disks; magneto-optical media; semiconductor memory devices, and hardware devices that are specially configured to store and perform program instructions, such as read-only memory devices (ROM) and random access memory (RAM). The data and program instructions of this invention may also be embodied on a carrier wave or other transport medium. Examples of program instructions include both machine code, such as produced by a compiler, and files containing higher level code that may be executed by the computer using an interpreter.

Figure 5:
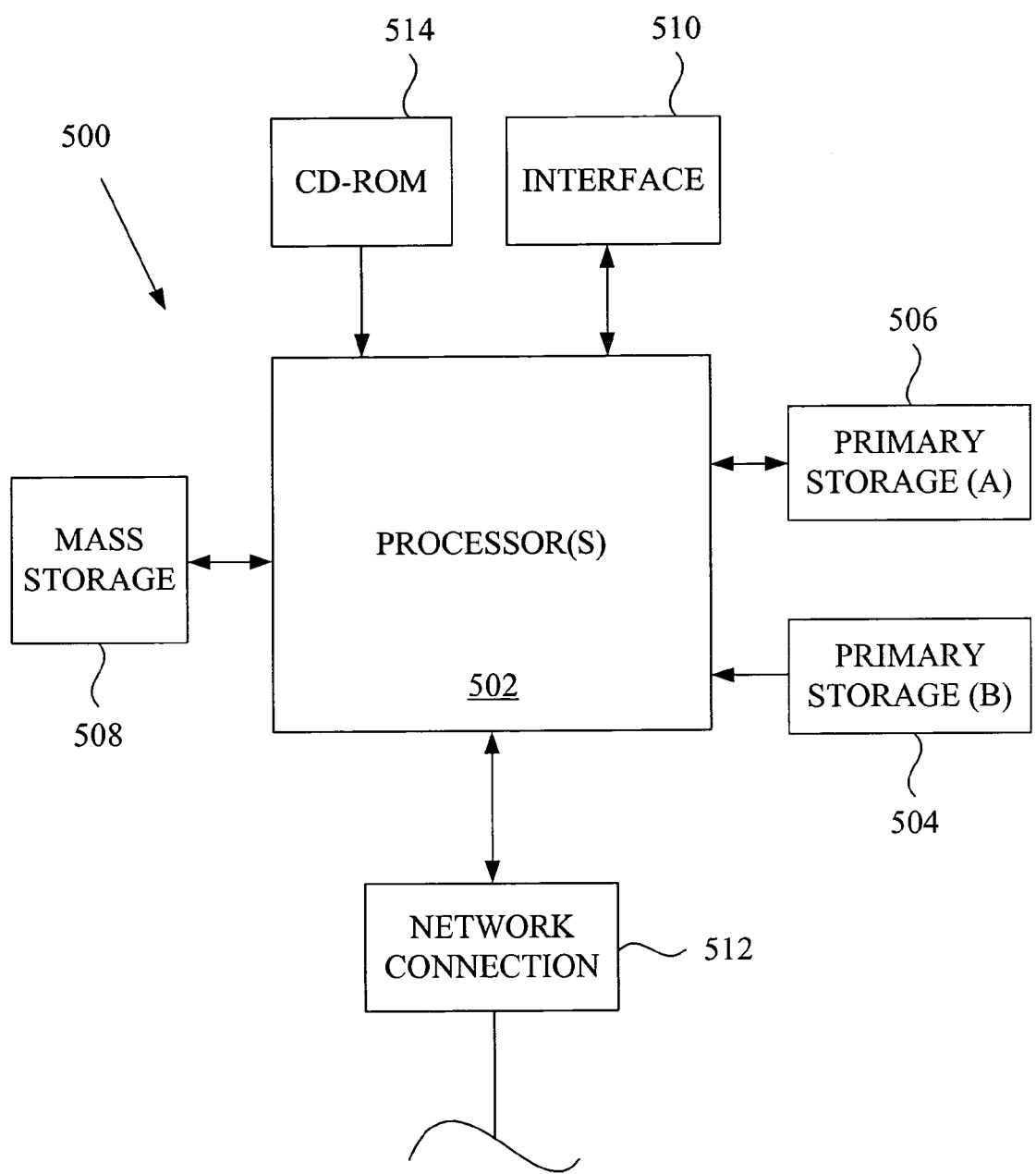
FIG. 5 is a diagrammatic representation of a computer system that can be used with the methods and apparatus of the present invention.

FIG. 5 illustrates a typical computer system that, when appropriately configured or designed, can serve as an image analysis apparatus of this invention. The computer system 500 includes any number of processors 502 (also referred to as central processing units, or CPUs) that are coupled to storage devices including primary storage 506 (typically a random access memory, or RAM), primary storage 504 (typically a read only memory, or ROM). CPU 502 may be of various types including microcontrollers and microprocessors such as programmable devices (e.g., CPLDs and FPGAs) and unprogrammable devices such as gate array ASICs or general purpose microprocessors. As is well known in the art, primary storage 504 acts to transfer data and instructions uni-directionally to the CPU and primary storage 506 is used typically to transfer data and instructions in a bi-directional manner. Both of these primary storage devices may include any suitable computer-readable media such as those described above. A mass storage device 508 is also coupled bi-directionally to CPU 502 and provides additional data storage capacity and may include any of the computer-readable media described above. Mass storage device 508 may be used to store programs, data and the like and is typically a secondary storage medium such as a hard disk. It will be appreciated that the information retained within the mass storage device 508, may, in appropriate cases, be incorporated in standard fashion as part of primary storage 506 as virtual memory. A specific mass storage device such as a CD-ROM 514 may also pass data uni-directionally to the CPU.

CPU 502 is also coupled to an interface 510 that connects to one or more input/output devices such as such as video monitors, track balls, mice, keyboards, microphones, touch-sensitive displays, transducer card readers, magnetic or paper tape readers, tablets, styluses, voice or handwriting recognizers, or other well-known input devices such as, of course, other computers. Finally, CPU 502 optionally may be coupled to an external device such as a database or a computer or telecommunications network using an external connection as shown generally at 512. With such a connection, it is contemplated that the CPU might receive information from the network, or might output information to the network in the course of performing the method steps described herein.

In one embodiment, the computer system 500 is directly coupled to an image acquisition system such as an optical imaging system that captures images of cells. Digital images from the image generating system are provided via interface 512 for image analysis by system 500. Alternatively, the images processed by system 500 are provided from an image storage source such as a database or other repository of cell images. Again, the images are provided via interface 512. Once in the image analysis apparatus 500, a memory device such as primary storage 506 or mass storage 508 buffers or stores, at least temporarily, digital images of the cell. With this data, the image analysis apparatus 500 can perform various image analysis operations such as classifying a cell according to a particular hepatotoxic pathology. To this end, the processor may perform various operations on the stored digital image. For example, it may analyze said image in manner that extracts values of one or more descriptors and classifies the cell as alive or dead or as exhibiting apoptosis, necrosis, steatosis, cholestasis, or some other pathology.

IX. Other Embodiments

The above discussion has focused on hepatocytes and hepatotoxic responses. Aspects of the invention extend beyond hepatotoxicity to toxicity in a variety of other cell lines, cell types, and tissues. Further, it may be employed to classify various non-hepatocyte cell types based on specific pathologies. Examples include myelosuppression using bone marrow cells, and nephrotoxicity using kidney cells.

Although the above generally describes the present invention according to specific exemplary processes and apparatus, various modifications can be made without departing from the spirit and/or scope of the present invention. Therefore, the present invention should not be construed as being limited to the specific forms shown in the appended figures and described above.

What is claimed is:

1. A method of assessing the hepatotoxicity of a stimulus, the method comprising:
    (a) exposing a hepatocyte culture to the stimulus;
    (b) imaging the hepatocytes;
    (c) analyzing an image of the hepatocytes to extract features characterizing the hepatocytes; and
    (d) classifying the stimulus by quantitatively evaluating the extracted features to identify one or more hepatotoxic pathologies resulting from the stimulus, wherein hepatotoxic pathology classifications include two or more of the following: necrosis, cholestasis, steatosis, fibrosis, apoptosis, and cirrhosis.

2. The method of claim 1 wherein multiple cultures are located on a single support structure, and wherein each in vitro culture is exposed to a distinct stimulus.

3. The method of claim 2, wherein at least two of the cultures are exposed to different quantities of the same stimulus.

4. The method of claim 2, wherein the support structure is a glass or plastic support.

5. The method of claim 2, wherein the support structure is a multiwell plate.

6. The method of claim 2, wherein hepatocytes are co-cultured with support cells.

7. The method of claim 1, wherein the stimulus is exposure to a chemical compound.

8. The method of claim 1, wherein the hepatocytes are transformed or immortalized cells.

9. The method of claim 8, wherein the transformed or immortalized cells have been modified to express one or more cytochrome P450 metabolizing enzymes.

10. The method of claim 1, wherein analyzing the image comprises segmenting the image to identify individual hepatocytes on the image.

11. The method of claim 1, wherein the features extracted in (c) comprise two or more of membrane permeability, enzyme activity, Golgi distribution, migration of cytochrome c from the mitrochondria, mitochondrial membrane potential, condensation, fragmentation and granularization of nuclei, accumulation of lipid containing vacuoles, bile production, actin morphology, and tight junction condition.

12. A method of identifying a necrotic hepatotoxic pathology resulting from a stimulus, the method comprising:
    (a) exposing a hepatocyte culture to the stimulus;
    (b) contacting the hepatocyte culture with markers for esterase activity and cell membrane permeability;
    (c) imaging the hepatocyte culture;
    (d) analyzing images of the hepactocyte culture to extract features relevant to necrosis;
    (e) identifying the average levels of esterase activity and cell membrane permeability for the hepatocyte culture based on the extracted features; and
    (f) characterizing the necrotic response of the hepatocyte culture to the stimulus based on the average levels of esterase activity and cell membrane permeability.

13. The method of claim 12, wherein the hepatocyte culture is characterized as necrotic if at least one of low esterase activity and high cell permeability is identified.

14. The method of claim 12, wherein the marker for esterase activity is calcein AM.

15. The method of claim 12, wherein the marker for cell membrane permeability is ethidium bromide homodimer.

16. A method of identifying an apoptotic hepatotoxic pathology resulting from a stimulus, the method comprising:
    (a) exposing a first and second hepatocyte culture to the stimulus;
    (b) performing a single step preparatory treatment of the first hepatocyte culture, wherein the single step preparatory treatment does not include washing the first hepatocyte culture;
    (c) performing a multi-step preparatory treatment of the second hepatocyte culture, wherein the multi-step preparatory treatment includes washing the first hepatocyte culture;
    (d) imaging the first and second hepatocyte cultures;
    (e) analyzing images of the first and second hepatocyte cultures to extract features relevant to apoptosis;
    (f) identifying condensation of the nuclei, cell adhesion, and average caspase-3 activity for the first and second hepatocyte cultures based on the extracted features; and
    (g) characterizing the apoptotic response of the first and second hepatocyte cultures to the stimulus based on the characteristics of the nuclei, cell adhesion, and average caspase-3 activity.

17. The method of claim 16, wherein the first and second hepatocyte cultures are characterized as apoptotic if at least one of condensation of the nuclei, lowering of cell adhesion, and increased caspase-3 activity are identified.

18. The method of claim 16, further comprising exposing at least one of the first and second hepatocyte cultures to a marker for DNA.

19. The method of claim 16, wherein cell adhesion is characterized by a washout coefficient.

* * * * *